United States Patent
Mohler

[11] Patent Number: 6,152,879
[45] Date of Patent: Nov. 28, 2000

[54] PASSIVE/NON-INVASIVE SYSTEMIC AND PULMONARY BLOOD PRESSURE MEASUREMENT

[75] Inventor: Sailor Mohler, Columbia, Md.

[73] Assignee: Primedica, LLC, Vienna, Va.

[21] Appl. No.: 09/167,242

[22] Filed: Oct. 6, 1998

Related U.S. Application Data

[62] Division of application No. 08/769,156, Dec. 18, 1996, Pat. No. 6,050,950.

[51] Int. Cl.⁷ .................................................. A61B 5/00
[52] U.S. Cl. ..................... 600/485; 600/500; 600/528; 600/586
[58] Field of Search .................... 600/485, 490, 600/493–497, 503, 528, 586

[56] References Cited

U.S. PATENT DOCUMENTS

| | | | |
|---|---|---|---|
| 4,378,022 | 3/1983 | Suobank et al. | 128/715 |
| 4,592,366 | 6/1986 | Sainomoto et al. | 128/680 |
| 4,594,731 | 6/1986 | Lewkowicz | 381/67 |
| 4,628,939 | 12/1986 | Little et al. | 128/696 |
| 4,792,145 | 12/1988 | Eisenberg et al. | 128/715 |
| 4,862,897 | 9/1989 | Eisenberg et al. | 128/715 |
| 4,928,705 | 5/1990 | Sekhar et al. | 128/773 |
| 4,967,760 | 11/1990 | Bennett, Jr. et al. | 128/715 |
| 5,012,815 | 5/1991 | Bennett, Jr. et al. | 128/715 |
| 5,025,809 | 6/1991 | Johnson et al. | 128/715 |
| 5,074,309 | 12/1991 | Gerdt | 128/715 |
| 5,205,295 | 4/1993 | Del Mar et al. | 128/711 |
| 5,218,969 | 6/1993 | Bredesen et al. | 600/528 |
| 5,301,679 | 4/1994 | Taylor | 600/528 |
| 5,337,752 | 8/1994 | Reeves | 128/700 |
| 5,365,937 | 11/1994 | Reeves et al. | 128/715 |
| 5,431,170 | 7/1995 | Mathews | 600/504 |
| 5,467,775 | 11/1995 | Callahan et al. | 128/715 |
| 5,492,129 | 2/1996 | Greenberger | 600/528 |
| 5,522,511 | 6/1996 | Kaspari et al. | 600/485 |
| 5,590,650 | 1/1997 | Genova | 128/630 |
| 5,595,188 | 1/1997 | Kassal | 128/773 |
| 5,638,823 | 6/1997 | Akay et al. | 600/504 |
| 5,680,867 | 10/1997 | Shimazu et al. | 600/500 |
| 5,687,738 | 11/1997 | Shapiro et al. | 600/528 |

FOREIGN PATENT DOCUMENTS 0 020 110 A1  5/1980  European Pat. Off. .......... A61B 5/02

OTHER PUBLICATIONS

Glower, et al., "Mechanical Correlates of the Third Heart Sound," 19 JACC (2) pp. 450–457 (Feb. 1992).

(List continued on next page.)

*Primary Examiner*—Robert L. Nasser
*Attorney, Agent, or Firm*—Roberts, Abokhair & Mardula

[57] ABSTRACT

An apparatus, operation and method for measurement of systemic and/or pulmonic blood pressure. The present invention offers a passive non-invasive method and system that can be used where measurement of systemic pressure with a traditional blood pressure cuff is contraindicated. The present invention also affords a means for early diagnosis and opportunity for intervention in patients with no symptoms or signs of elevated pulmonary blood pressure that can be performed as part of a routine physical exam. The present invention accomplishes this non-invasive measurement through detection, identification and characterization of the second heart sound acoustic signature associated with heart valve closure. An apparatus for measuring systemic and/or pulmonic blood pressure in accordance with the present invention includes a sensor assembly comprising a housing, an electronic module, a shock dampener, a mounting means, a transducer, an acoustic coupling and a back cover. The sensor assembly is connected to a data acquisition module which in turn is connected to a signal processing means, a remote connection means and a monitor. An improved acoustic coupling is disclosed that provides low-loss acoustic transmission coupling between the skin of the patient and the detector.

27 Claims, 13 Drawing Sheets

OTHER PUBLICATIONS

Thakor, "Applications of Adaptive Filtering to ECG Analysis: Noise Cancellation and Arrhythmia Detection," 38 IEEE Transaction on Biomedical Engineering (8) pp. 785–794 (Aug. 1991).

Bulgrin et al., "Time Frequency Analysis of Heart Sounds," Scientific Computing and Automation, pp. 15–19 (Aug., 1994).

Jansen, "Monitoring of the Ballistocardiogram with the Static Charge Sensitive Bed," 38 IEEE Transaction on Biomedical Engineering (8) pp. 748–751 (Aug. 1991).

Akay et al., "Application of Adaptive FTF/FAEST Zero Tracking Filters to Noninvasive Characterization of the Sound Pattern Caused by Coronary Artery Stenosis Before and After Angioplasty," 21 Annals of Biomedical Engineering, pp. 9–17 (1993).

Wood et al., "Time–Frequency Transforms: A New Approach to First Heart Sound Frequency Dynamics," 39 IEEE Transaction on Biomedical Engineering (7) pp. 730–740 (Jul., 1992).

Jamous et al., "Optimal time–window duration for Computing Time/Frequency Representations of Normal Phonocardiograms in Dogs," Medical & Biological Engineering & Computing, pp. 503–508 (Sep. 1992).

Rangayyan, et al., "Phonocardiogram Signal Analysis: A Review," 15 CRC Critical Reviews in Biomedical Engineering (3) pp. 211–236 (1988).

Colley, et al., "The Fetal Phonogram: A Measure of Fetal Activity," The Lancet pp. 931–934 (Apr., 1986).

Salzmann, et al., "Der Herzschall—eine mathematische Transformation des Blutdrucks?" Schweiz. Rundschau Med. (PRAXIX) 81, Nr 39 (1992).

Nagel, "New Diagnostic and Technical Aspects of Fetal Phonocardiography," 23 Eur. J. Obstet. Gynecol. Reprod. Biol. pp. 295–303, 305 (1986).

Khadra et al., "The Wavelet Transform and its Applications to Phonocardiogram Signal Analysis," 16 Med. Inform. (3), pp. 271–277 (1991).

Picard, "Phonocardiogram Spectral Analysis Simulator of Mitral Valve Prostheses," 15 J. Med. Eng. & Tech. (6) pp. 222–231 (Dec. 1991).

Obaidat, "Phonocardiogram Signal Analysis: Techniques and Performance Comparison," 17 Jn. Med. Eng. & Techn. (6) pp. 221–227.

Lehner et al., "A Three–Channel Microcomputer System for Segmentation and Characterization of the Phonocardiogram," BME34 IEEE Transaction on Biomedical Engineering (6) pp. 485–489 (Jun., 1987).

Abe et al., "Measurement of Left Atrial Systolic Time Intervals in Hypertensive patients Using both Doppler Echocardiography: Relation to Fourth Heart Sound and Left Ventricular Wall Thickness," 11 JACC (4) pp. 800–805 (Apr. 1988).

Luisada et al., "Assessment of Left Ventricular Function by Noninvasive Methods," 32 Adv. Cardiol, pp. 111–141 (1985).

Ofili, et al., "Coronary Flow Velocity Dynamics in Normal and Diseased Arteries," 71 American Jn. Cardiology pp. 3D–9D (May 20, 1993).

Donnerstein, "Continuous Spectral Analysis of Heart Murmers for Evauating Stenotic Cardiac Lesions," 64 American J, Cardiology pp. 625–630 (Sep. 1989).

Miller, et al., "Spectral Analysis of Arterial Bruits (Phonoangiography): Experimental Validation," 61 Circulation (3) pp. 515–520 (Mar. 1980).

Clarke, "Spectral Energy of the First Heart Sound in Acute Myocardial Ischemia," 57 Circulation (3) pp. 593–598 (Mar. 1978).

Anderson, et al., "Modern Approaches to the Diagnosis of Coronary Artery Disease," American Heaqrt Journal, pp. 1312–1323 (May, 1982).

Khalifa, et al., "Characterization and Evolution of Poststenotic Flow Disturbances," 14 J. Biomechanics (5) pp. 279–295 ((1980).

Akay et al., "Noninvasive Characterization of the Sound Pattern Caused by Coronary Artery Stenosis Using FTF/FAEST Zero Tracking Filters: Normal/Abnormal Study," 21 Annals of Biomedical Engineering, pp. 175–182 (1993).

Oort, et al., "The Vibratory Innocent Heart Murmur in Schoolchildren: Difference in Auscultory Findings Between School Medical officers and a Pediatric Cardiologist," 15 Pediatr. Cardiol. pp. 282–287 (1994).

Dalton, "Fetal Phonocardiography," 23 Eur. J. Obstet. Gynecol. Reprod. Biol., pp. 305 (1986).

Perini, et al., "Body Position Affects the Power Spectrum of Heart Rate Variability During Dynamic Exercise," 66 Eur. J. Appl. Physiol., pp. 207–213 (1993).

Strony, et al., "Analysis of Shear Stress and Hemodynamic Factors in a Model of Coronary Artery Stenosis and Thrombosis," 265 Am. J. Physiol., pp. H1787–H1796 (1993).

Laude, et al., "Effect of Breathing Pattern on Blood Pressure and Heart Rate Oscillations in Humans," 20 Clinical & Experimental Pharmacology and Physiology, pp. 619–626 (1993).

Patterson, et al., "Impedance Cardiography Using Band and Regional Electrodes in Supine, Sitting, and During Exercise," 38 IEEE Transaction on Biomedical Engineering (5) pp. 393–400 (May 1991).

Hamilton et al., "Compression of the Ambulatory ECG by Average Beat Subtraction and Residual Differencing," 38 IEEE Transaction on Biomedical Engineering (3) pp. 253–259 (Mar. 1991).

Hamilton et al., "Theoretical and Experimental Rate Distortion Performance in Compression of Ambulatory ECG's," 38 IEEE Transaction on Biomedical Engineering (3) pp. 260–266 (Mar. 1991).

Akay, "Noninvasive Acoustical Detection of Coronary Artery Disease: A Comparative Study of Signal Processing Methods," 40 IEEE Transaction on Biomedical Engineering (6) pp. 571–578 (Jun., 1993).

Akay et al., "Acoustical Detection of Coronary Occlusions Using Neural Networks," 15 J. Biomed. Eng pp. 469–473 (1993).

"A New, Non–Invasive Test for the Detection of 'Silent' Coronary Disease," North Texas Preventive Imaging, pp. 1–6.

Huikuri, et al., "Frequency Domain Measures of Heart Rate Variability Before the Onset of Nonsustained and Sustained Ventricular Tachycardia in Patients With Coronary Artery Disease," 87 Circulation (4), pp. 1220–1228 (Apr., 1993).

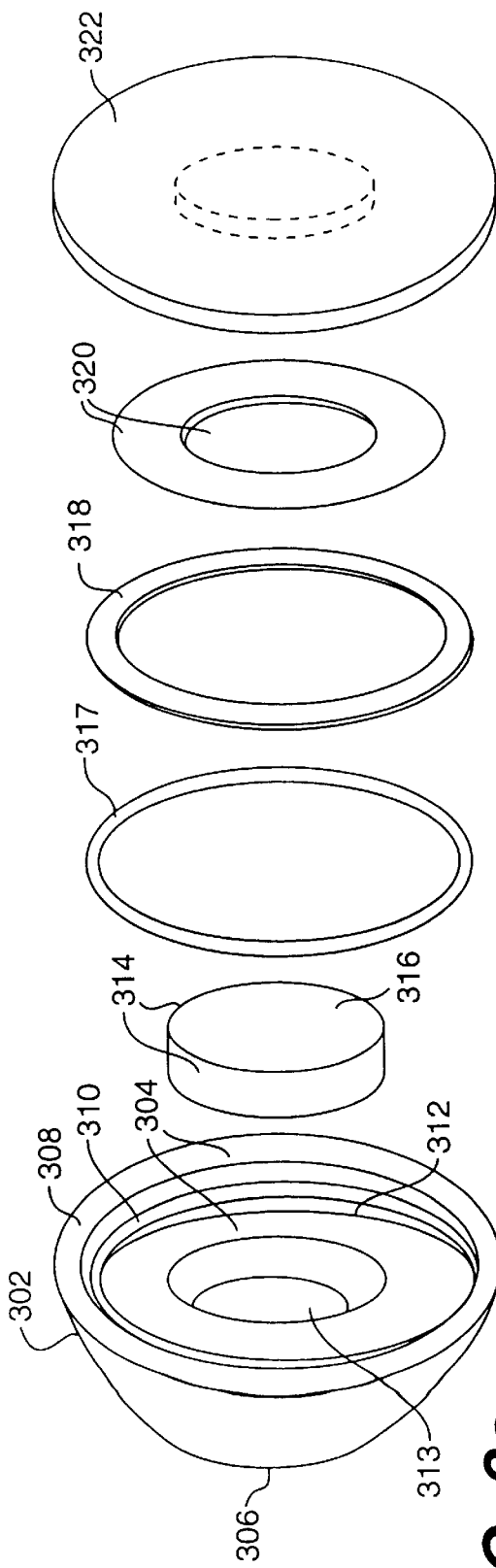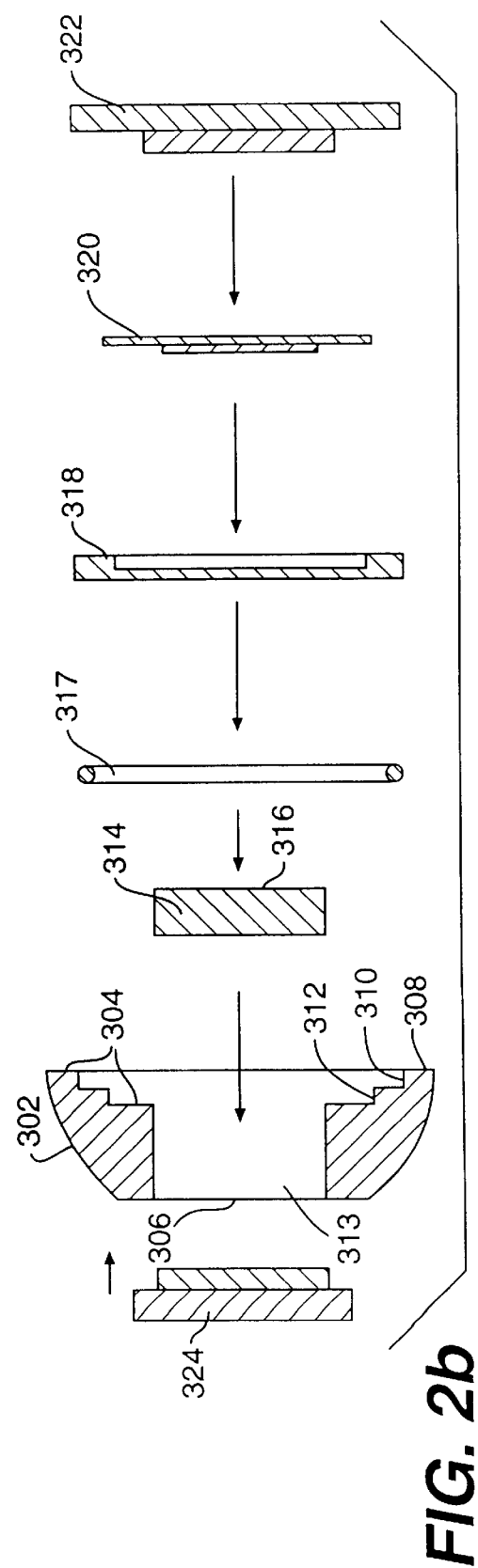
FIG. 2a
FIG. 2b

PASSIVE/NON-INVASIVE SYSTEMIC AND PULMONARY BLOOD PRESSURE MEASUREMENT

RELATED APPLICATION INFORMATION

This application is a divisional of U.S. patent application Ser. No. 08/769,156 filed Dec. 18, 1996 by Sailor Mohler now U.S. Pat. No. 6,050,950.

FIELD OF THE INVENTION

This application is a divisional of co-pending application Ser. No. 08/769156 filed on Dec. 18, 1996, disclosure of which is herein incorporated by reference in its entirety.

This invention relates generally to an apparatus, operation and method for measurement of blood pressure. In particular, this invention relates to an apparatus, operation and method for the detection, identification and characterization of sounds relating to either systemic or pulmonary blood pressure through the use of sonospectrography.

BACKGROUND OF THE INVENTION

Blood pressure is the force exerted by the blood against the inner walls of blood vessels. Blood pressure determination is an important diagnostic tool. The blood vessels that comprise the vascular system can be grouped into two main divisions, a systemic circuit and a pulmonary circuit. In the systemic circuit, high blood pressure may indicate the presence of arteriosclerosis or other vascular disease, while low blood pressure may indicate shock or blood loss. Detection and measurement of elevated pulmonary blood pressure is a key diagnostic indicator for a number of pulmonary diseases, such as: cystic fibrosis, pleuresy, lung pulmonary diseases, and pulmonary impedance. Early diagnosis of these diseases greatly assists in symptom mitigation and improved patient quality of life.

The systemic circuit includes the aorta and its branches that deliver oxygenated blood to all body tissues, as well as the companion system of veins returning blood to the right atrium. Freshly oxygenated blood received by the left atrium is forced into the systemic circuit by the contraction of the left ventricle. When the left ventricle contracts, the mitral valve closes, and the only exit is through the aortic valve into the aorta.

The peripheral nature of certain systemic circuit arteries in the body extremities allows for the traditional indirect measurement of the systolic and diastolic pressures with a sphygmomanometer blood pressure cuff. While this method is effective for many patients, use of the traditional blood pressure cuff on an extremity may be contraindicated for patients suffering from any number of problems including severe extremity trauma, or burns. In patients where use of the traditional blood pressure cuff is contraindicated, there is no reliable alternative method of monitoring blood pressure. This is extremely important in trauma patients where prompt detection of blood pressure changes are needed to counteract the effects of shock or large blood loss.

The pulmonic circuit provides for blood circulation from the right ventricle through the pulmonary valve into the pulmonary artery. The pulmonary artery extends upward and posteriorly from the heart, dividing into right and left branches which serve the right and left lungs, respectively. Within the lungs the right and left branches of the pulmonary artery divide repeatedly giving rise to arterioles that continue into the capillary networks associated with the walls of the alveoli. Gas exchange occurs as the blood moves through these capillaries, so that when the blood enters the venules of the pulmonary circuit, it is well oxygenated and poor in carbon dioxide. The pulmonary venules merge forming small veins, which in turn converge forming larger veins. Four pulmonary veins return oxygenated blood to the left atrium, thereby completing the pulmonic circuit.

None of the arteries of the pulmonic system are located in extremities and therefore measurement of pulmonic system pressure with a blood pressure cuff is not possible.

At present, the only reliable method for measuring pulmonic system blood pressure is through use of an invasive blood pressure catheter that is inserted directly into the pulmonary artery. This diagnostic procedure has a substantial degree of risk and is expensive, its use is thus generally seen as an unjustified procedure in patients without other symptoms.

The physician may attempt to detect and differentiate the abnormal sounds that occur with elevated blood pressure using traditional auscultation. Closure of the aortic and pulmonary semilunar heart valves generate a sound component that is in the audio frequency range. As the systemic or pulmonic blood pressure increases, the frequency components of the related heart valve also increase. This increased frequency audio component is not present in a healthy patient. However, aural detection of this frequency increase is extremely difficult because the physician must determine the absolute frequency of the audio component of the heart valve of interest. Additionally, the sounds are very weak and heavily contaminated with noise from other patient heart sounds, other normal patient body sounds and external ambient noise in the room. Further, the audio component of the aortic and pulmonary semilunar heart valves are heavily attenuated as they pass through the patient's chest and chest wall.

A need exists for a non-invasive, low cost and reliable means for determining systemic blood pressure in those situations where traditional means are contraindicated. A need also exists for a non-invasive, low cost and reliable means for determining pulmonary blood pressure.

DESCRIPTION OF RELATED ART

As mentioned, the sounds related to systemic and pulmonary heart pressure are difficult to discern. U.S. Pat. No. 4,528,690 to Sedgwick; U.S. Pat. No. 3,790,712 to Andries; and U.S. Pat. No. 3,160,708 to Andries et al. disclose relatively simple electronic stethoscopes as methods for amplification of the sounds in an attempt to raise the subaudible components into the audible range. However, simple amplification of the entire frequency spectrum, as disclosed, does not help in determining the absolute frequency of the heart valve sounds, or in detecting the subtle changes of this frequency that occur with changes in blood pressure.

To this end, U.S. Pat. No. 4,594,731 to Lewkowicz and U.S. Pat. No. 5,347,583 to Dieken et al. disclose various forms of selective filtering or signal processing on the audio signal in the electronic stethoscope. Lewkowicz discloses a means for shifting the entire detected spectrum of sounds upward while expanding the bandwidth so that they are more easily perceived by the listener. Dieken et al. discloses an electronic stethoscope having a greater volume of acoustic space and thereby improving low frequency response.

The electronic stethoscope provides a moderate improvement over conventional methods of auscultation. However, information remains in audio form only and is transient; the physician is unable to visualize the data and either freeze the display or focus on a particular element of the signal retrieved. To accommodate that deficiency, the technique of phonocardiography, which is the mechanical or electronic registration of heart sounds with graphic display, is used. U.S. Pat. No. 5,218,969 to Bredesen et al.; U.S. Pat. No. 5,213,108 to Bredesen et al.; U.S. Pat. No. 5,012,815 to Bennett, Jr. et al.; U.S. Pat. No. 4,967,760 to Bennett, Jr. et al.; U.S. Pat. No. 4,991,581 to Andries; and U.S. Pat. No. 4,679,570 to Lund et al. disclose phonocardiography with signal processing and visual/audio output. U.S. Pat. No. 5,301,679 to Taylor; and U.S. Pat. No. 4,792,145 to Eisenberg et al. disclose phonocardiography with signal processing and visual display.

The process of phonocardiography as commonly known in the art, acquires acoustic data through an air conduction microphone strapped to a patients chest, and provides the physician with a strip chart recording of this acoustic data. The strip chart is generally created at a rate of 100 mm/second. As this method is generally used, with the exception of the created strip chart, data is not stored. Thus, it is not possible to manipulate and/or process the data post acquisition. In addition, phonocardiography does not provide the sensitivity needed to monitor softer physiological sounds such as the closure of the semilunar valves and blood flow through the circulatory system.

As previously noted, one problem in traditional auscultation is ambient noise from the room in which the examination is occurring, which reduces the signal-to-noise ratio of the sounds of interest. U.S. Pat. No. 4,672,977 to Kroll discloses a method for automatic lung sound cancellation and provides visual and audio output. U.S. Pat. No. 5,309,922 to Schecter et al. discloses a method for cancellation of ambient noise to enhance respiratory sounds and provides visual and audio output. U.S. Pat. No. 5,492,129 to Greenberger discloses a method for reducing general ambient noise and provides audio output.

U.S. Pat. No. 5,036,857 to Semmlow et al. discloses a method of phonocardiography with piezoelectric transducer. Semmlow specifically recommends against Fast Fourier Transformation analysis of the phonocardiography data and relies on processing by other means. U.S. Pat. No. 5,109,863 to Semmlow et al.; and U.S. Pat. No. 5,035,247 issued to Heimann also disclose piezoelectric transducers.

U.S. Pat. No. 5,002,060 to Nedivi, discloses both heart and respiratory sensors, with Fast Fourier Transformation analysis. In the technique disclosed by Nedivi the sensors are not physically attached to the patient. Thus the sensors are not capable of detecting the low intensity sound of the aortic and pulmonary semilunar heart valves.

Devices currently known in the art do not provide either a means of determining systemic blood pressure where use of a blood pressure cuff is contraindicated, or a low risk, non-invasive means of determining pulmonic blood pressure. Additionally, the related art does not provide the level of aural sensitivity needed to reliably detect the sounds of the aortic and pulmonary semilunar heart valves and determine the precise frequency of these sounds.

What is needed is a safe, sensitive and noninvasive means of measuring systemic and/or pulmonic blood pressure. This is accomplished through the present invention. Through the use of sonospectrography, a procedure based on integral spectral analysis techniques, systemic pressure can be monitored in conditions where traditional auscultation is contraindicated. Additionally, sonospectrography can be used to monitor pulmonic pressure in an inexpensive, noninvasive and low risk manner, allowing for the early detection of conditions such as cystic fibrosis, pleuresy, lung pulmonary diseases and pulmonary impedance. Sonospectrography is defined as the separation and arrangement of the frequency components of acoustic signals in terms of energy or time.

Further embodiments of the present invention provide a means of detecting physiological sounds, such as sounds emitted by the heart and other body organs as well as sounds related to the flow of blood through the circulatory system. Analysis of these sounds can be used to determine systemic and pulmonary blood pressure, monitor anesthesiology, determine cardiac output, monitor the circulation of diabetic individuals, and monitor fetal heartbeat as well as detect conditions such as aneurysms, arterial occlusions, arthritic decrepitation, phlebitis, venous thrombosis, intravascular blood clotting and carotid artery disease.

SUMMARY OF THE INVENTION

It is therefore an object of the present invention to provide an apparatus, operation and method for the detection and analysis of physiological sounds, such as sounds emitted by the heart and other body organs as well as sounds related to the flow of blood through the circulatory system.

It is a further object of the present invention to provide an apparatus, operation and method to be used to determine systemic and pulmonary blood pressure, monitor anesthesiology, determine cardiac output, monitor the circulation of diabetic individuals, and monitor fetal heartbeat as well as detect conditions such as aneurysms, arterial occlusions, arthritic decrepitation, phlebitis, venous thrombosis, intravascular clotting and carotid artery disease.

It is a further object of the present invention to provide this apparatus, operation and method through the use of sonospectrography.

It is a further object of the present invention to provide this apparatus, operation and method through a synchronized and coordinated combination of sonospectrography and electrocardiogram signals.

It is a further object of the present invention to provide this apparatus, operation and method through visual display means that provide insight to the subtle characteristics of the acoustic signature.

It is a farther object of the present invention to provide this apparatus, operation and method through selective time and frequency windowing of the acoustic signals.

It is a further object of the present invention to provide this apparatus, operation and method through real-time signal processing or recorded-signal post processing.

It is a further object of the present invention to provide this apparatus, operation and method through use of single or multiple transducers.

It is a further object of the present invention to provide this apparatus, operation and method through a computer assisted search algorithm to identify optimal placement of the transducer(s) on the patient's chest wall.

It is a further object of the present invention to provide this apparatus, operation and method in office environments with moderate to high ambient noise levels, through adaptive noise cancellation techniques.

It is a further object of the present invention to provide this apparatus, operation and method in a form that provides for dynamic template building to facilitate disease detection and identification.

It is a further object of the present invention to provide this apparatus, operation and method through neural network techniques.

It is a further object of the present invention to provide an acoustic coupling that minimizes signal loss between the subject-detector interface and allows for the detection of sounds heretofore undetectable in a normal room environment.

It is a further object of the present invention to extend the ability of clinicians to analyze sounds which are lower in amplitude than those detectable by the unaided ear.

It is a further object of the present invention to extend the ability of clinicians to analyze sounds which are lower in frequency than those detectable by typical auscultation techniques.

It is a further object of the present invention to increase detection of a specified frequency range through the use of a tailored bandpass amplifier.

It is a further object of the present invention to provide a means for data storage, data manipulation and data transmission.

It is a further object of the present invention to provide this apparatus, operation and method through advanced processing of acoustic signatures in the time and frequency domain to isolate and display the sound components associated with pulmonary and/or aortic heart valve closure.

It is a further object of the present invention to provide an apparatus, operation and method that is suitable for routine physical examination screening and early diagnosis of elevated pulmonic blood pressure thereby providing an opportunity for early intervention to enhance the patient's productive life.

It is a further object of the present invention to provide an apparatus, operation and method that is suitable for monitoring of systemic blood pressure in patients where use of a traditional blood pressure cuff is contraindicated.

These and other objects of the present invention will become obvious to those skilled in the art upon review of the following disclosure.

An apparatus for determining blood pressure in accordance with the present invention includes a sensor assembly comprising a housing, an electronic module, a shock dampener, a mounting means, a piezoelectric transducer, an acoustic coupling and a back cover. The sensor assembly is connected to a data acquisition module which in turn is connected to a signal processing means. The signal processing means is connected to an electronic storage means, a hard copy reproduction means, a remote connection means and a monitor. In an alternative embodiment of the invention a plurality of sensor assemblies are connected to the data acquisition module. In another alternative embodiment of the invention a means for determining an electrocardiogram is connected to the signal processing means. In yet another alternative embodiment of the invention, data acquisition module is connected to high-fidelity earphones.

The operation for determining blood pressure in accordance with the present invention includes:

1) performing start-up procedures;
2) acquiring physiologic signals;
3) acquiring ambient or background signals;
4) processing and subtracting ambient signals from physiologic signals;
5) conditioning and processing resultant data;
6) subjecting the conditioned and processed data to Fast Fourier Transformation;
7) passing the time domain components of the data through a time domain correlator and feature extraction process;
8) passing the frequency domain components of the data through a frequency domain correlator and feature extraction process;
9) comparing the time domain output and the frequency domain output to a reference pattern and feature library;
10) determining whether the time domain output and frequency domain output match known disease modalities;
11) determining whether a disease modality is indicated;
12) updating the reference pattern and feature library; and
13) providing the information regarding the disease modality to the physician so that a treatment regimen may commence.

The method for determining blood pressure in accordance with the present invention includes monitoring the sounds of the aortic and/or the pulmonary semilunar valves. Where one wishes to determine systemic pressure, the aortic semilunar valve is monitored. This is done by placing the acoustic coupling of the sensor assembly adjacent to the patient's skin at the traditional auscultation point for the aortic valve. Where one wishes to monitor pulmonary pressure, the pulmonary semilunar valve is monitored. This is done by placing the acoustic coupling of the sensor assembly in contact with the patient's skin at the traditional auscultation point for the pulmonic valve. Detected signals are manipulated in the same fashion noted in the "operation" of the present invention. The signals may be viewed and analyzed by medical personnel at any number of points during this data manipulation process to allow for the implementation of a treatment regimen. Where the sound emitted by either semilunar valve is of a higher than normal frequency, this is indicative of increased blood pressure in the corresponding circuit; that is, an increased frequency emitted by the aortic semilunar valve is indicative of higher than normal systemic blood pressure, while an increased frequency being emitted by the pulmonary semilunar valve is indicative of higher than normal pulmonary blood pressure.

BRIEF DESCRIPTION OF THE DRAWINGS

FIG. 2a depicts an exploded, oblique view of the sensor assembly.

FIG. 2b depicts an exploded, side view of the sensor assembly.

DETAILED DESCRIPTION

The present invention provides an apparatus, operation and method to passively and noninvasively measure systemic and pulmonic blood pressure through detection, identification and characterization of the acoustic signature associated with heart valve closure.

APPARATUS

Figure 1:
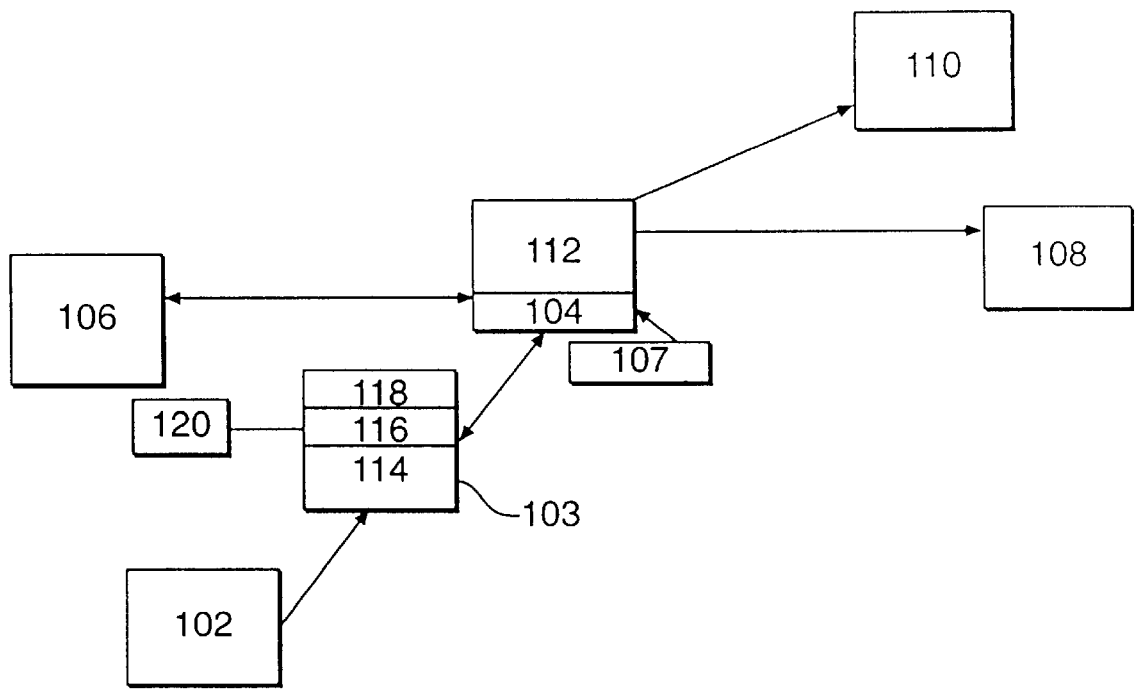
FIG. 1 is a schematic representation of the overall architecture and user interface of the present invention.

Referring to FIG. 1, the overall architecture of the present invention is described. Patient physiologic signals, such as acoustic vibrations or electrical impulses, are detected by sensor assembly 102. In an alternative embodiment a plurality of sensor assemblies can be used to either simultaneously obtain signals from various locations of the body or to simultaneously obtain signals from both the patient and the environment. Sensor assembly 102 is connected to data acquisition means 103.

Data acquisition means 103 comprises preamplifier 114, audio amplifier 116, and analog-to-digital converter 118. Preamplifier 114 electronically isolates the transducer, detects the electronic signals, and sends them to audio amplifier 116 and to analog-to-digital converter 118. Audio amplifier 116 drives one or more sets of high-fidelity earphones 120. Analog-to-digital converter 118 samples the analog signal and converts it to a binary number for each time sample. Data acquisition means 103 is connected to signal processing means 104.

Signal processing means 104 is a general-purpose microprocessor. Signal processing means 104, also has means for video display of information, such as monitor 112. Signal processing means 104 is connected to electronic data storage means 106, operator input means 107, hard copy reproduction means 108 and remote connection means 110.

Various types of electronic data storage are known to those skilled in the art. In alternative embodiments electronic data storage means 106 comprises: internal hard disk drive, external hard disk drive, floppy disks, digital audio tape, magneto-optical storage or CD ROM. Likewise, various types of operator input means are known to those skilled in the art. In alternative embodiments operator input means 107 comprises: keyboard, mouse, voice detector or other means. Hard copy reproduction means 108 provides copies of images displayed on monitor 112 for purposes such as maintaining medical records, assisting consultations, and assisting data processing and review. Remote connection means 110 is a modem. In alternative embodiments, the system of the present invention may be directly linked to a network via a network interface card or other suitable means. Thus a modem may not always be necessary.

In an alternative sensor assembly embodiment, sensor assembly 102 can detect both physiologic and background signals. In another alternative sensor assembly embodiment, one side of sensor assembly 102 comprises an audio transducer which is in contact with the skin while a second audio transducer on the opposite side faces away from the patient. This second transducer is designed to acquire ambient sounds in synchronism with the sounds reaching the transducer in contact with the patient's skin to reject common mode signals reaching both transducers. By adding the environmental signals out of phase with the signals acquired from the patient, the sounds in common to both transducers are effectively canceled. In yet another alternative sensor assembly embodiment the target frequency range for data acquisition is about 200 to 2000 Hz. In another alternative sensor assembly embodiment, the target frequency range for signal acquisition is about 400 hertz.

In an alternative preamplifier embodiment, preamplifier 114 demonstrates low-noise data acquisition and proper impedance matching.

In an alternative analog-to-digital converter embodiment analog-to-digital converter 118 has a sample rate about 4 to 48 Khz. In yet another alternative analog-to-digital converter embodiment, analog-to-digital converter 118 has a sample rate of about 44 Khz. In another alternative analog-to-digital converter embodiment, analog-to-digital converter 118 has a resolution of about 16 bits. In yet another alternative analog-to-digital converter embodiment, analog-to-digital converter 118 has a linearity about ±0.005 percent of full scale. In another alternative analog-to-digital converter embodiment, analog-to-digital converter 118 has a sample length of about one to sixty seconds. In yet another alternative analog-to-digital converter embodiment, analog-to-digital converter 118 has an operator selectable sample length.

In an alternative earphones embodiment, earphones 120 have separate volume controls.

In an alternative signal processing means embodiment, signal processing means 104 is a computer with a central processing unit. In another alternative signal processing means embodiment, signal processing means 104 is an IBM compatible personal computer using an INTEL processor (386, 486, Pentium), having a minimum of 8 MB RAM memory and a minimum hard disk size of 500 MB. In yet another alternative signal processing means embodiment, signal processing means 104 is a Macintosh PowerPC.

In an alternative monitor embodiment, monitor 112 has a minimum display size of 600×400 pixels and a minimum monitor 112 display depth of eight bits. In yet another alternative monitor embodiment, monitor 112 is a high resolution EGA or VGA color display monitor.

In an alternative signal processing means embodiment, signal processing means 104 comprises a sound card. In another alternative signal processing means embodiment, the sound card comprises a "Tahiti" multiple channel computer sound card manufactured by Turtle Beach, although sound cards such as the Pro Audio 1b (Media Vision) can also be used.

In an alternative hard copy reproduction means embodiment, hard copy reproduction means 108, is a printer. In another alternative hard copy reproduction means embodiment, hard copy reproduction means 108 is a printer capable of generating a variety of different graphic displays. In yet another alternative hard copy reproduction means embodiment, hard copy reproduction means 108 is a laser printer.

In an alternative remote connection means embodiment, remote connection means 110 is an internal or external, high speed modem. In another alternative remote connection means embodiment, remote connection means 110 has a speed of at least 14.4 kilobytes per second.

Referring to FIG. 2a, an oblique view of an embodiment of sensor assembly 102 is shown. FIG. 2b depicts a side view of an embodiment of sensor assembly 102. Housing 302 comprises a sound deadening material having sufficient mass to dampen high frequency ambient disturbances and hold the sensor assembly in contact with the patient through gravity. Housing 302 has housing front 304 and housing back 306. Rim 308 is located on the periphery of housing front 304. First indentation 310 runs parallel and adjacent to the inside of rim 308. Second indentation 312 runs parallel and adjacent to the inside of first indentation 310. Bore 312 is approximately centrally located within second indentation 312 and is shaped and sized in conformity to the shape and size of electronic module 314. Electronic module 314 nests within bore 312 of housing 302. As will be further discussed, signal detection and processing circuitry are incorporated within electronic module 314.

Shock dampener 316 is positioned adjacent to first indentation 310. Mounting means 318 is positioned adjacent to shock dampener 316. Transducer 320 is positioned within mounting means 318. Transducer 320 converts detected signals into electronic signals. Acoustic coupling 322 is positioned adjacent to transducer 320. Acoustic coupling 322 serves to dilinearize excitation response and reduce dynamic range.

Once assembled, housing 302 is closed to the ambient environment with back cover 324. Sensor assembly 102 comprising all the individual sensor elements, is assembled and sealed to form a single complete unit.

In an alternative housing embodiment, housing 302 is composed of nickel plated aluminum, but can be any material having sufficient mass to dampen high frequency ambient disturbances and hold the sensor in contact with the patient through gravity.

In an alternative sensor assembly embodiment, when electronic module 314 nests within bore 312 of housing 302, top 316 of electronic module 314 is flush with second indentation 312.

In an alternative shock dampener embodiment shock dampener 316 is an "O" ring.

In an alternative mounting means embodiment, mounting means 318 is a plastic mounting ring.

In an alternative transducer embodiment, transducer 320 is a piezoelectric disk. In another alternative transducer embodiment, transducer 320 has a high impedance. In yet another alternative transducer embodiment, transducer 320 has an impedance of about 470 Kohms. In another alternative transducer embodiment, transducer 320 has high efficiency as compared with conventional electromagnet type speakers. In yet another alternative transducer embodiment, transducer 320 is ultra thin and lightweight. In another alternative transducer embodiment, transducer 320 has a frequency range of about 500–20,000 Hz. In yet another alternative transducer embodiment, transducer 320 has a capacitance at 120 Hz of about 60±30% nF. In another alternative transducer embodiment, transducer 320 current leakage is limited to about one micro ampere.

In an alternative acoustic coupling embodiment, acoustic coupling 322 is impedance matched, and serves to provide a low-loss acoustic transmission coupling between the skin of the patient and transducer 320, thereby minimizing signal loss across the subject-detector interface. In another alternative acoustic coupling embodiment, acoustic coupling 322 is a parametric acoustic transconductor. In yet another acoustic coupling embodiment, acoustic coupling 322 has a high conduction coefficient. In another alternative acoustic coupling embodiment, acoustic coupling 322 is made of latex foam. In yet another alternative acoustic coupling embodiment, acoustic coupling 322 is logarithmically attenuated, having low transmission at low frequencies and high transmission at high frequencies.

Figure 3:
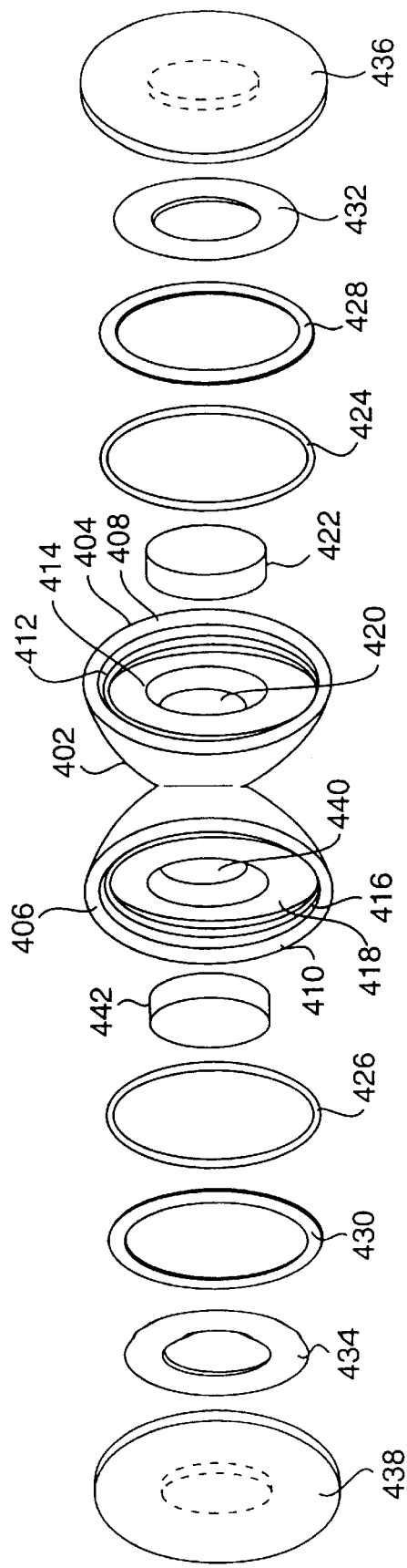
FIG. 3 depicts an exploded, oblique view of an alternative embodiment of the sensor assembly.

Referring to FIG. 3 an oblique exploded view of an alternative embodiment of sensor assembly 102 is shown. Housing 402 comprises a sound deadening material having sufficient mass to dampen high frequency ambient disturbances and hold the sensor assembly in contact with the patient through gravity. Housing 402 has housing front 404 and housing back 406. First rim 408 is located on the periphery of housing front 404. Second rim 410 is located on the periphery of housing back 406. First indentation 412 runs parallel and adjacent to the inside of first rim 408. Second indentation 414 runs parallel and adjacent to the inside of first indentation 412. Third indentation 416 runs parallel and adjacent to the inside of second rim 410. Fourth indentation 418 runs parallel and adjacent to the inside of third indentation 416. First bore 420 is approximately centrally located within second indentation 414 and is shaped and sized in conformity to the shape and size of first electronic module 422. Second bore 440 is approximately centrally located within fourth indentation 418 and is shaped and sized in conformity to the shape and size of second electronic module 442. First electronic module 422 nests within first bore 420 of housing 402. Second electronic module 442 nests within second bore 440 of housing 402. As will be further discussed, signal detection and processing circuitry are incorporated within first and second electronic module 422, 442.

First shock dampener 424 is positioned adjacent to first indentation 412. Second shock dampener 426 is positioned adjacent to third indentation 416. First mounting means 428 is positioned adjacent to first shock dampener 424. Second mounting means 430 is positioned adjacent to second shock dampener 426. First transducer 432 is positioned within first mounting means 428. Second transducer 434 is positioned within second mounting means 430. First transducer 432, converts detected physiologic signals into electronic signals. Second transducer 434, converts detected environmental or background signals into electronic signals. First acoustic coupling 436 is positioned adjacent to first transducer 432. Second acoustic coupling 438 is positioned adjacent to second transducer 434. First and second acoustic coupling 436, 438 serve to dilinearize excitation response and reduce dynamic range.

In an alternative housing embodiment, housing 402 is composed of nickel plated aluminum.

In an alternative shock dampener embodiment, first and second shock dampener 424, 426 is an "O" ring.

In an alternative mounting means embodiment, first and second mounting means 428, 430 is a plastic mounting ring.

In an alternative transducer embodiment, first and second transducer 432, 434 is a piezoelectric disk. In another alternative transducer embodiment, first and second transducer 432, 434 has a high impedance. In yet another alternative transducer embodiment, first and second transducer 432, 434 has an impedance of about 470 Kohms. In another alternative transducer embodiment, first and second transducer 434, 434 has high efficiency as compared with conventional electromagnet type speakers. In yet another alternative transducer embodiment, first and second transducer 432, 434 is ultra thin and lightweight. In another alternative transducer embodiment, first and second transducer 432, 434 has a frequency range of about 5–2,000 Hz. In yet another alternative transducer embodiment, first and second transducer 432, 434 has a capacitance at 120 Hz of about 60±30% nF. In another alternative transducer embodiment, first and second transducer 432, 434 current leakage is limited to about one micro ampere.

In an alternative acoustic coupling embodiment, first and second acoustic coupling 436, 438, is impedance matched, and serves to provide a low-loss acoustic transmission coupling between the skin of the patient and first transducer 432, thereby minimizing signal loss across the subject-detector interface. In another alternative acoustic coupling embodiment, first and second acoustic coupling 436, 438 is a parametric acoustic transconductor. In yet another acoustic coupling embodiment, first and second acoustic coupling 436, 438 has a high conduction coefficient. In another alternative acoustic coupling embodiment, first and second acoustic coupling 436, 438 is made of latex foam. In yet another alternative acoustic coupling embodiment, acoustic coupling 322 is logarithmically attenuated, having low transmission at low frequencies and high transmission at high frequencies.

Figure 4:
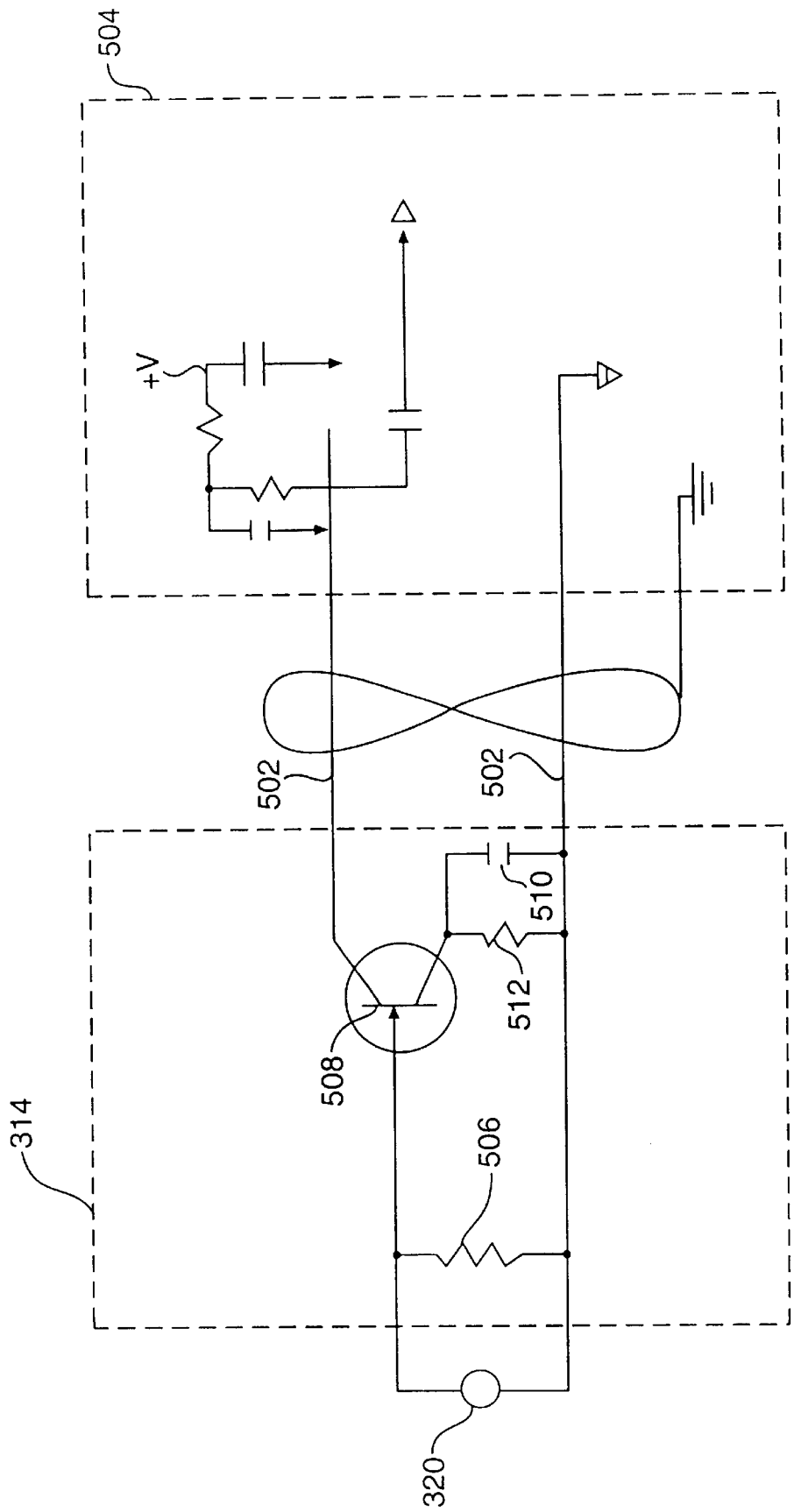
FIG. 4 depicts a circuit diagram of the electronic module, data cable and data acquisition module.

Referring to FIG. 4, electronic module 314, transducer 320, data cable 502, and data acquisition module 504 of the present invention are shown in schematic form. In combination, first resistor 506, semiconductor device 508, second resistor 510, and first capacitor 512 comprise electronic module 314. Electronic module 314 performs functions such as signal amplification, and filtering. Transducer 320 is connected in parallel with first resistor 506, second resistor 510, first capacitor 512, and semiconductor 508. Semiconductor 508 serves to modulate current. First capacitor 512 provides gain and source decoupling for semiconductor 508.

In an alternative first resistor embodiment, first resistor 506 provides a matching load to transducer 320. In another alternative first resistor embodiment first resistor 506 has a resistance of 470 Kohms.

In an alternative second resistor embodiment, second resistor 510 is about 10 Kohms.

In an alternative semiconductor embodiment, semiconductor 508 is field effect transistor. In another alternative semiconductor embodiment, semiconductor 508 is a field effect transistor with an N-type base.

In an alternative first capacitor embodiment, first capacitor 512 is 60 microfarads and is connected to ground.

Figure 5:
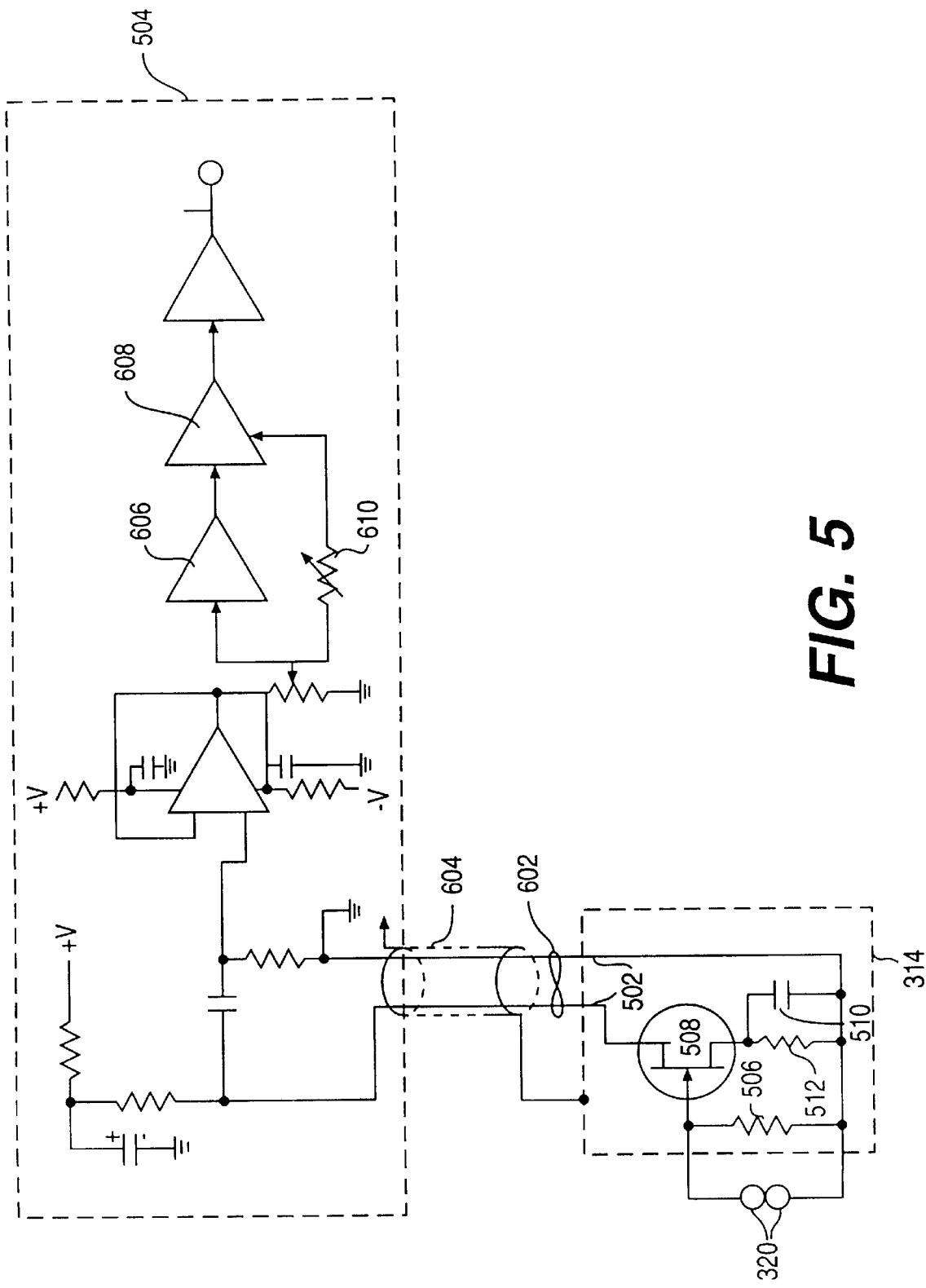
FIG. 5 depicts a circuit diagram of greater detail, comprising the electronic module, data cable and data acquisition module.

FIG. 5 depicts a circuit diagram of the electronic module, data cable and data acquisition module in greater detail. The circuit comprises electronic module 314, transducer 320, data cable 502, and data acquisition module 504. Data cable 502 couples electronic module 314 to data acquisition module 504. Data acquisition module 504 comprises an amplifier. As depicted in FIG. 5, highpass filter 606 is followed by lowpass filter 608 having a DC injection point. The amount of DC injection is made variable by value selection of variable resistor 610. In an alternative value selection embodiment, value selection is determined by the practitioner. In yet another alternative value selection embodiment, value selection is determined automatically by the signal processing means in conformity with predetermined parameters.

In an alternative data cable embodiment, data cable 502 is twisted pair 602, wherein two insulated wires are twisted forming a flexible line without the use of spacers. In another alternative data cable embodiment, data cable 502 is shielded pair 604, wherein two parallel conductors are separated from each other and surrounded by a solid dielectric. In this alternative embodiment, the conductors are contained within a copper-braid tubing that acts as a shield. The assembly is covered with a rubber or flexible composition coating to protect the line against moisture and friction. There are two advantages of this alternative embodiment: (1) the capacitance between each conductor and ground is uniform along the entire length of the line; and (2) the wires are shielded against pickup of stray electric fields. In yet another alternative embodiment shielded pair 604 data cable 502 is connected to sensor housing 610 and to ground as a means for reducing electrical noise and increasing patient safety.

In an alternative data acquisition module embodiment, data acquisition module 504 has a low frequency response from about 10 Hz to a crossover point at 100 Hz, rising to a level 20 dB higher from about 600 Hz to 2 KHZ, then declining steadily beyond that point. In another alternative data acquisition module embodiment, data acquisition module 504 comprises a voltage gain, variable from zero to fifty, allowing recovery of low-level sounds from 600 to about 2000 Hz while preserving the ability to measure low-frequency signals having a relatively high amplitude, without amplifier saturation.

Figure 6:
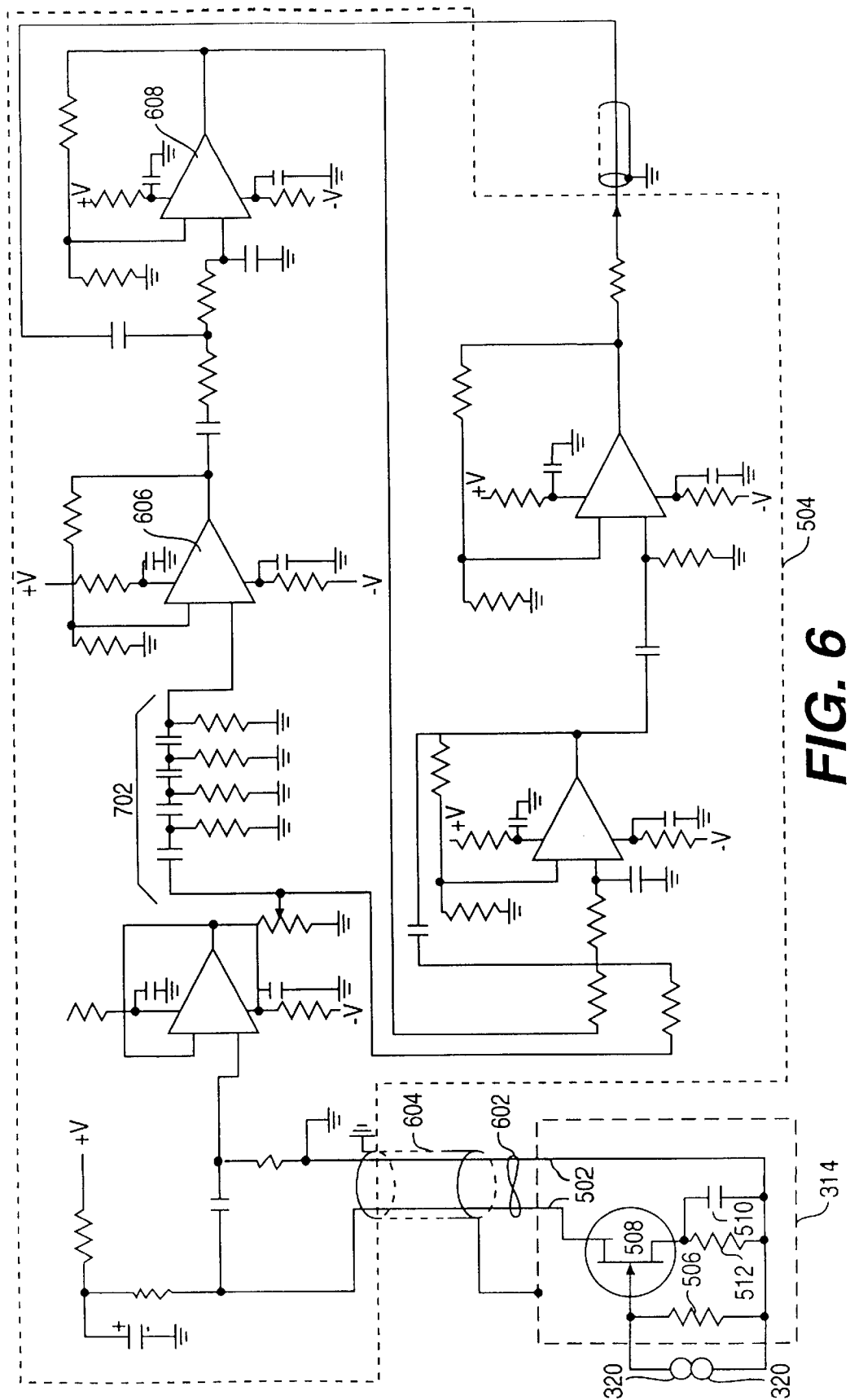
FIG. 6 depicts a circuit diagram of still greater detail, comprising the electronic module, data cable and data acquisition module.

In an alternative highpass filter embodiment, highpass filter 606 has a gain of about 7, and lowpass filter 608 drives an output amplifier with a gain of about 7. In another alternative highpass filter embodiment the overall voltage gain available with the gain potentiometer at maximum will be about 50. An advantage of this alternative embodiment is the ability to reject a narrow range of frequencies in a notch caused by the phase delay in the components of highpass filter 606. In an alternative highpass filter embodiment this notch is set at 100 Hz. In another alternative highpass filter embodiment this notch is set at about 50–60 Hz, thereby providing a measure of hum rejection FIG. 6 depicts a circuit diagram of the electronic module, data cable and data acquisition module in greater detail. The circuit comprises electronic module 314, transducer 320, data cable 502, and data acquisition module 504. Three stage resistor/capacitor network 702 gives a total of about 180 degrees of phase shift at a design frequency of about 100 Hz that is related to the combined resistor/capacitor time constants of the network. Field effect transistor 508 input is AC-coupled to the four-pole lowpass filter 608 formed by a single 747-type operational amplifier pair.

Figure 7:
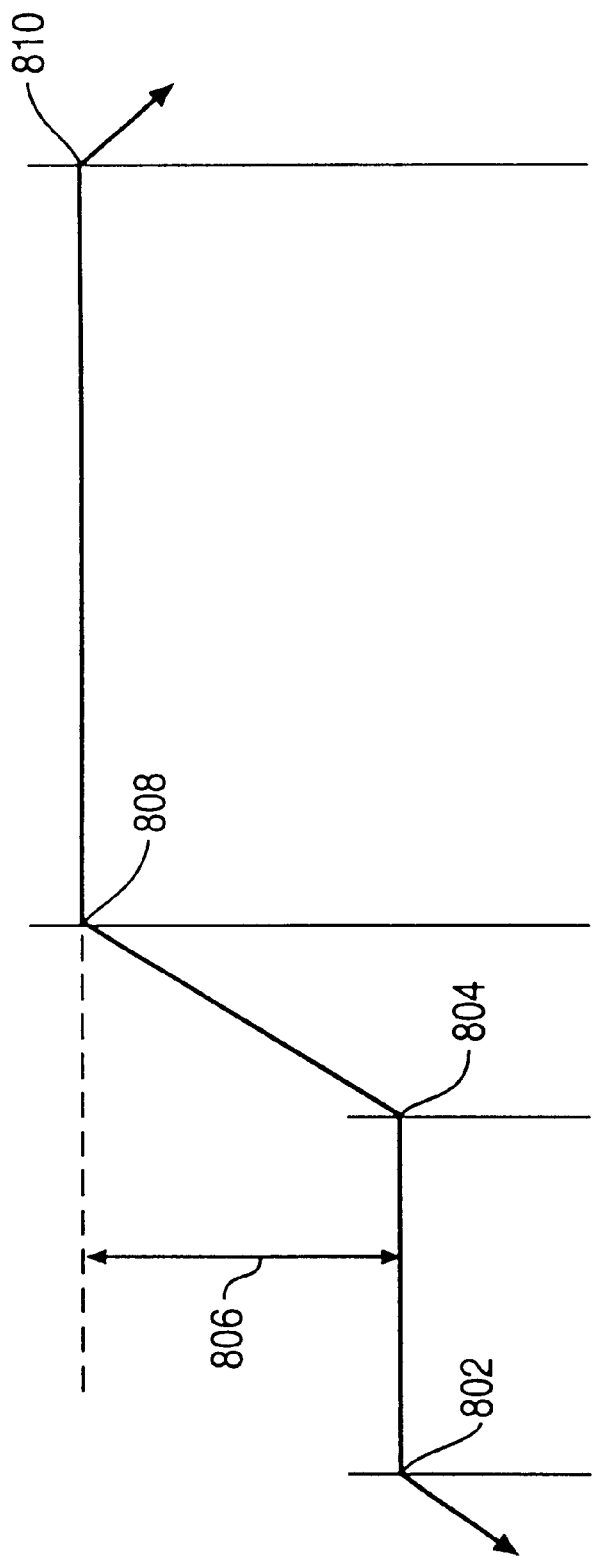
FIGS. 7 and 8 depict the frequency response of a tailored bandpass amplifier.

FIG. 7 depicts an idealized shape of an amplifier having low-frequency response from first point 802 to crossover point 804 and having higher frequency response of predetermined level 806, from second point 808 to third point 810. In an alternative embodiment, first point 802 is about 10 Hz, crossover point 804 is about 100 Hz, predetermined level 806 is about 20 dB, second point 808 is about 600 Hz and third point 810 is about 2 Khz. In yet another alternative embodiment, crossover point 804 is about 60 Hz.

Figure 8:
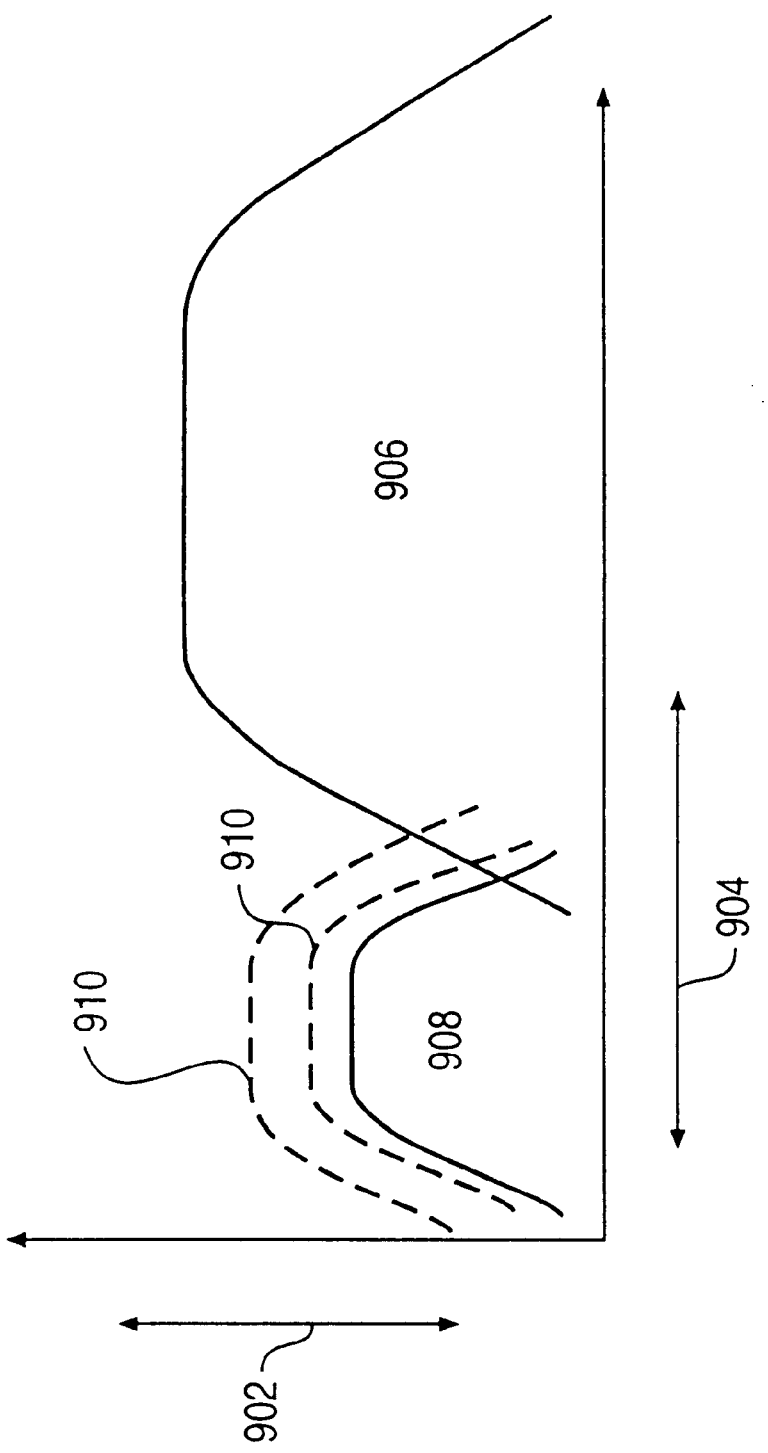

FIG. 8 further depicts the response of the tailored bandpass amplifier, plotting amplitude 902 vs. frequency 904 of basic heart sounds 906 and sounds of interest 908. In alternative embodiments, the response of sounds of interest 908 may be set at varying levels 910.

Figure 9:
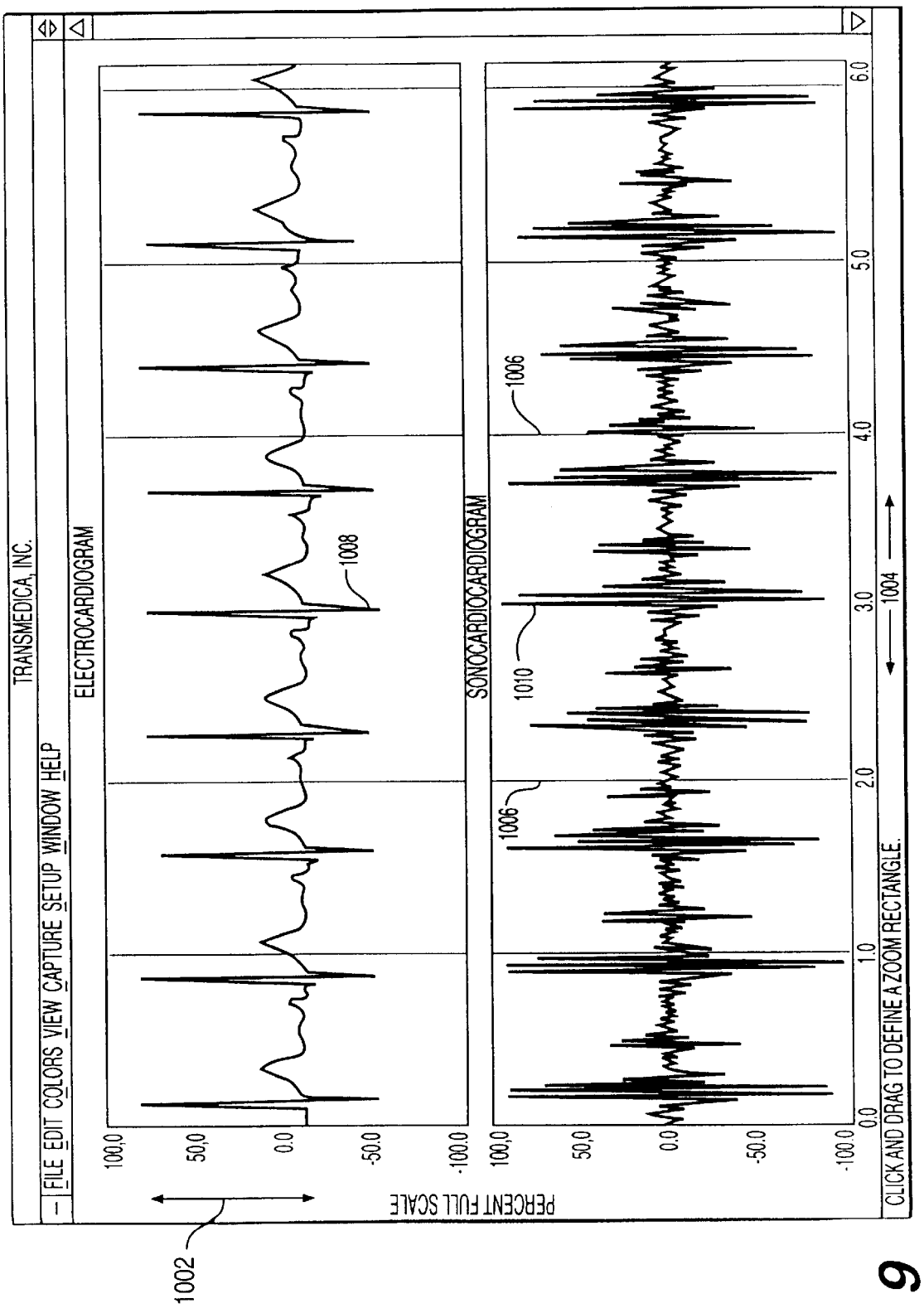
FIG. 9 illustrates the simultaneous display of ECG and acoustic signal data.

FIG. 9 depicts the simultaneous display of electrocardiogram and sonospectrography data. In the simultaneous display mode, the present invention provides for plotting electrocardiogram data and sonospectrography data as a function of intensity 1002 and time 1004, with digital markers 1006 to allow the visual correlation of points of signal activity that may be common to both signals. As an example, the electrocardiogram pulse at 1008 can be visually correlated with a select part of the acoustic signal 1010 and differentially measured to within 23 millionths of a second. This allows an operator who may be less familiar with acoustic signatures to correlate the electrocardiogram signal, which may be well understood, with the acoustic signal.

Figure 10A:
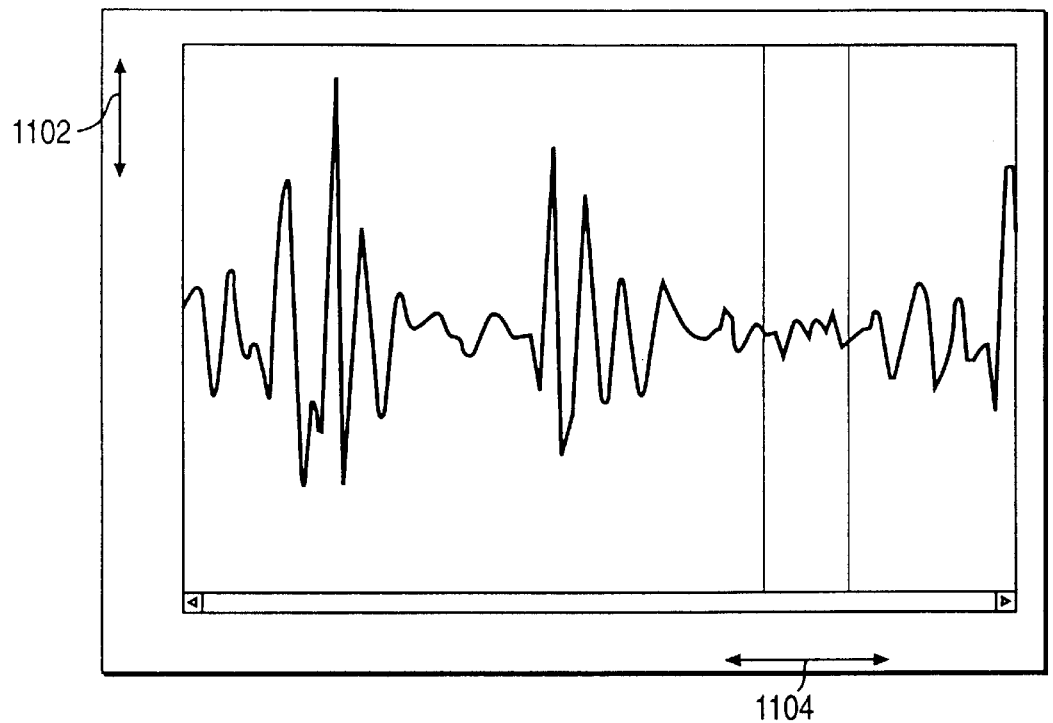
FIG. 10a illustrates an acoustic amplitude vs. time display mode.
Figure 10B:
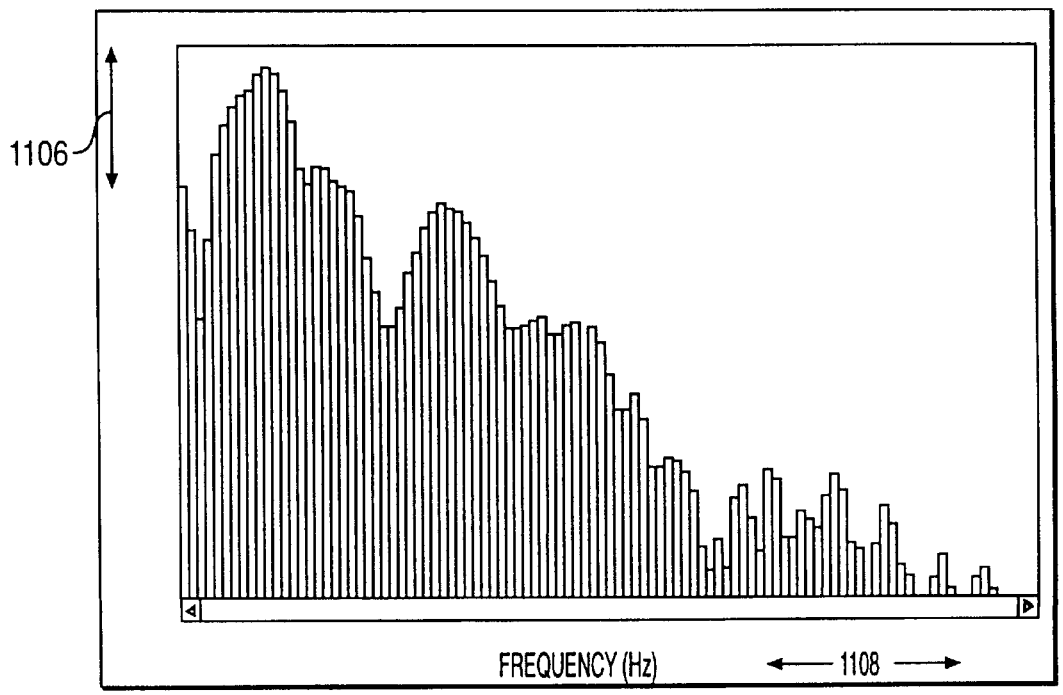
FIG. 10b illustrates a relative amplitude vs. frequency display mode.
Figure 10C:
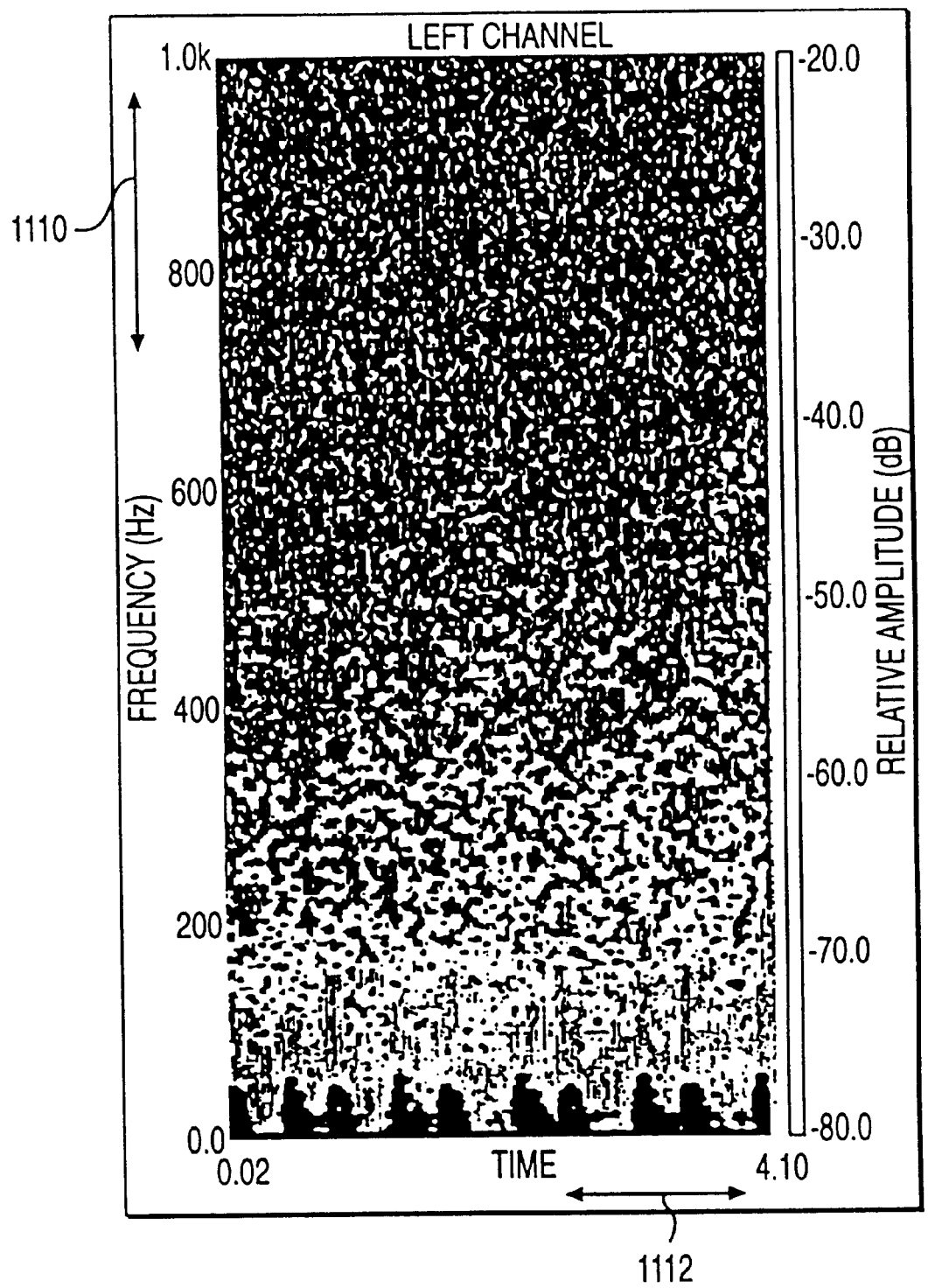
FIG. 10c illustrates a frequency vs. time display mode.

Referring to FIGS. 10a, 10b, and 10c, the display methodology of the present invention is shown. The present invention provides a means to simultaneously display the signal of interest in a variety of different forms. In FIG. 10a, the signal of interest of the present invention is presented as a simple time series, with acoustic amplitude 1102 on the vertical scale and time 1104 on the horizontal scale. In FIG. 10b, the signal of interest of the present invention is presented as a time and frequency display, with relative amplitude 1106 of each slice of the frequency spectrum on the vertical scale and frequency spectrum 1108 on the horizontal display. In FIG. 10c, the signal of interest of the present invention is presented with frequency 1110 on the vertical axis, time 1112 on the horizontal axis, and relative amplitude plotted in different color hues (not shown) and/or grey scale intensity.

Having thus described the basic concept of the apparatus of the invention, it will be readily apparent to those skilled in the art that the foregoing detailed disclosure is intended to be presented by way of example only, and is not limiting. Various alterations, improvements and modifications will occur and are intended to those skilled in the art, but are not expressly stated herein. For example, while cardiovascular monitoring is a key aspect of the invention, the techniques described herein are equally applicable to the monitoring of other body organs and regions of the body of both humans and animals and thus may also find utility in the veterinary sciences. These modifications, alterations and improvements are intended to be suggested hereby, and are within the spirit and scope of the invention.

OPERATION

Figure 11:
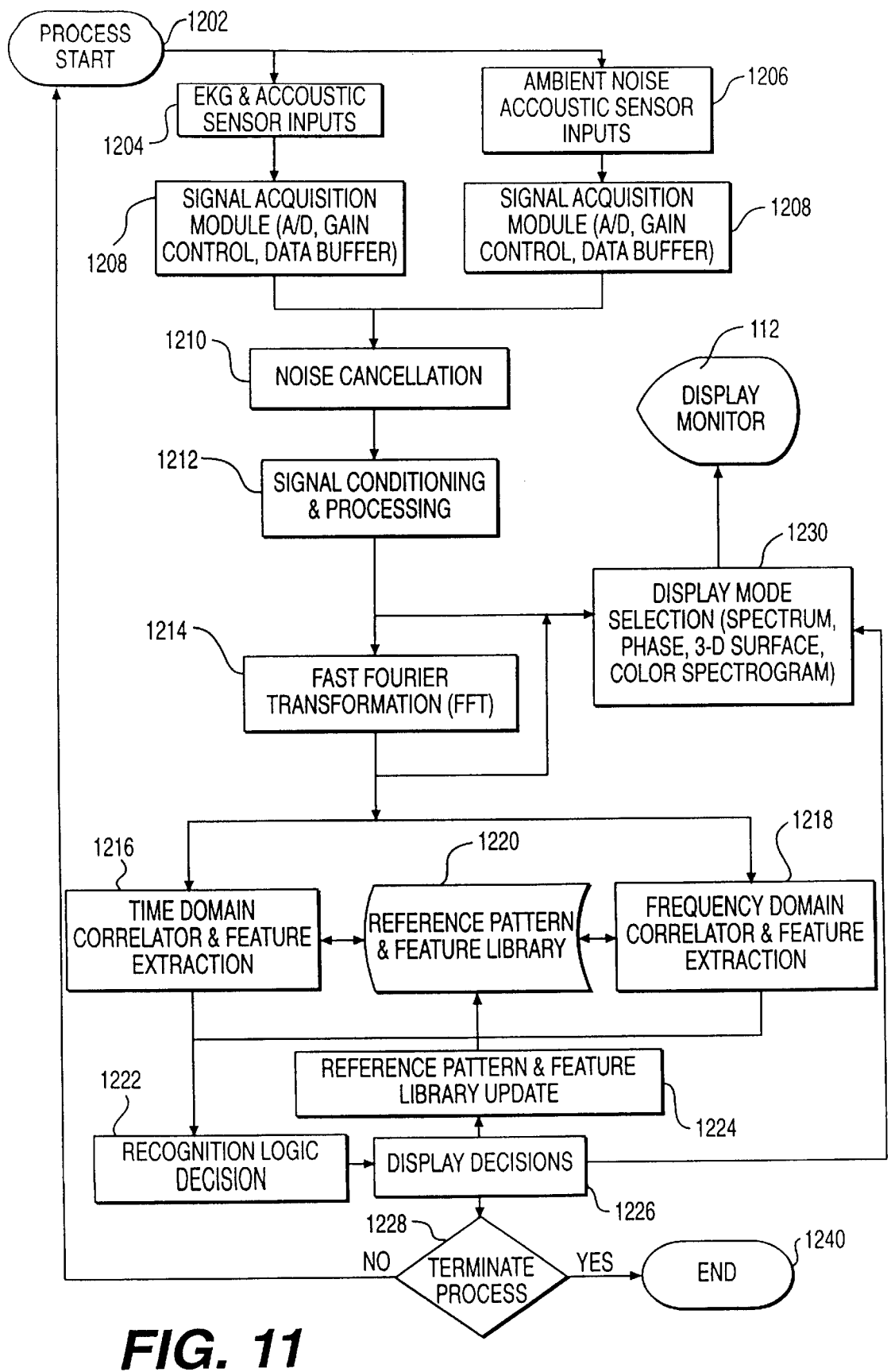
FIG. 11 is a flow chart illustrating the operation of the present invention.

FIG. 11 depicts the operation of the apparatus of the present invention with associated hardware and software. At step 1202, start-up procedures are performed such as initialization, calibration, sensor selection, patient parameter input, and buffer clearing, among others. Upon completion of these start-up procedures steps 1204 and 1206 are initiated. At step 1204, sensor 102 provides patient physiologic signals for signal processing. In an alternative embodiment, sensor 102 can include electrocardiogram sensors and acoustic sensors. At step 1206 acoustic sensors are used to detect background or ambient noise.

Next, at step 1208, the detected signals are passed to individual data acquisition modules which contain means for signal filtering, impedance matching, amplification, and buffering. These functions are performed by the components of the circuitry illustrated in FIGS. 4–6.

At step 1210, the signals from the ambient noise acoustic sensor acquired in step 1206, are processed and subtracted from the signals from the desired sensor of step 1204 in a noise cancellation process to reduce the effect of ambient noise from the patient's environment.

At step 1212, the signal undergoes additional signal conditioning and processing. The purpose of this conditioning step is to convert the analog signal to digital, provide adjustable decimation with a sampling rate suitable to avoid biasing, provide adjustable smoothing, averaging and peak holding. In an alternative embodiment the signal conditioning and processing of step 1212 is performed by a sound card which typically has the following capabilities: (1) a sample rate selectable from about 4K to 44K; (2) a sample size of about 16 bits; (3) capable of analog to digital conversion; (4) capable of digital to analog conversion; and (5) possesses IBM computer bus compatibility such as ISA, EISA, PCI, etc. In yet another alternative embodiment the sound card used comprises a "Tahiti" multiple channel Sound Card manufactured by Turtle Beach. Step 1230 allows for the intermediate output and display of the desired signal following the signal conditioning and processing of step 1212. The display is accomplished by selection of a desired display mode and subsequent display on the monitor 112. The output of step 1212 is of a time series and is suitable for display selection as in FIG. 10a.

At step 1214, the digitized and conditioned data is subjected to a sliding fast Fourier transformation. The output of step 1214 is of time and frequency and is suitable for display selection according to FIGS. 10b or 10c.

At step 1216, time domain components of the data passes through a time domain correlator and feature extraction process. In a similar fashion, in step 1218, the frequency domain components of the data passes through a frequency domain correlator and feature extractor. In step 1220, the outputs from the time domain correlator and feature extraction process of step 1216 and the frequency domain correlator and feature extractor of step 1218 are compared to a reference pattern and feature library, to determine whether the features contained within the signal of interest match known disease modalities as recorded and maintained within the reference pattern and feature library.

At step 1222, the outputs from the time domain correlator and feature extraction process of step 1216, the frequency domain correlator and feature extractor process of step 1218 and the results from the reference pattern and feature library comparison of step 1220 are subjected to a recognition logic decision, where a determination is made as to whether a disease or adverse condition is indicated. At step 1224, the new disease modality indicated in the recognition logic decision of step 1222 is then used to update the reference pattern and feature library of step 1220. In step 1226 a desired display mode such as depicted in FIGS. 10a, 10b and 10c is chosen for subsequent display on the monitor 112. At step 1228 the process is either terminated at step 1240 or begun anew at step 1202.

The preceding descriptions of the operation of the present invention are merely illustrative. In various embodiments of the disclosed invention operational steps may be added, eliminated, performed in parallel or performed in a differing order.

METHOD

Sonospectrography can be used as a primary source of auscultatory information in a routine physical examination or in population screening. Sonospectrography can be used in cardiology and general medicine for the detection of functional and organic disorders of the heart such as congenital defects, valve function, diseases of the pericardium and myocardium and systemic and pulmonary hypertension. Sonospectrography can also be used as a traditional stethoscope to capture sounds generated by other organs, such as the lungs, trachea, larynx, liver and carotid arteries.

Elevated blood pressure has a number of causes. Regardless of the cause, however, recent testing at the Uniformed Services University of Health Sciences shows that there is a change in the frequency spectrum of both the aortic and pulmonary semilunar valve sounds that is directly correlated to change in blood pressure of the associated systemic or pulmonary circulatory system. This correlation was shown to be both measurable and repeatable in testing on animals having systemic and pulmonary circulatory systems comparable to the human system.

Elevated blood pressure increases back pressure at associated heart valves. This increased back pressure results in more rapid closure of the heart valves and a resultant audible "snap" of the valve leaflets. The acoustic signature that is associated with those heart valve sounds has elevated frequency components as compared to the signature associated with heart valves operating under normal blood pressures. As the blood pressure increases, this frequency component also increases. It has been determined that this change in the frequency component is transitory and returns to normal when the blood pressure returns to normal.

Thus, where the sound emitted by the aortic semilunar valve is of an increased frequency, this is indicative of higher systemic blood pressure. Similarly, where the sound emitted by the pulmonary semilunar valve is of an increased frequency, this is indicative of higher pulmonic blood pressure. Through the use of the apparatus of the present invention, it is possible to detect and record sounds originating from the aortic and pulmonary semilunar valves.

In practice, a sensor assembly is placed in contact with the patient. One side of the sensor assembly contains an acoustic coupler that is placed in contact with the patient's skin at the traditional auscultation point for the valve of interest, while a second acoustic coupler on the opposite side faces away from the patient. This second acoustic coupler is designed to acquire background sounds in synchronism with the acoustic coupler in contact with the patient's skin to reject common mode signals reaching both couplers. While breathing normally the sounds of the aortic and/or pulmonary semilunar valves are acquired, preamplified and sent to a plurality of locations.

One analog signal is sent directly to an audio amplifier and high fidelity earphones. A second analog signal is sent through a gain control potentiometer to an analog to digital converter. The data is digitized and displayed in real time on a monitor. Visual feedback from the monitor allows a precise setting of the gain control by the physician for the optimum acquisition of data. In an alternative embodiment, an electronic strip chart is used in the precise setting of the gain control. The physician adjusts gain control to maximize the dynamic range of the captured signal.

In one embodiment, sounds are filtered normally. In an alternative embodiment, sounds are filtered to de-emphasize interfering responses prior to being sent to the earphones or the analog to digital converter. Data can be stored digitally, recalled for future analysis or transmitted to another location.

Figure 12:
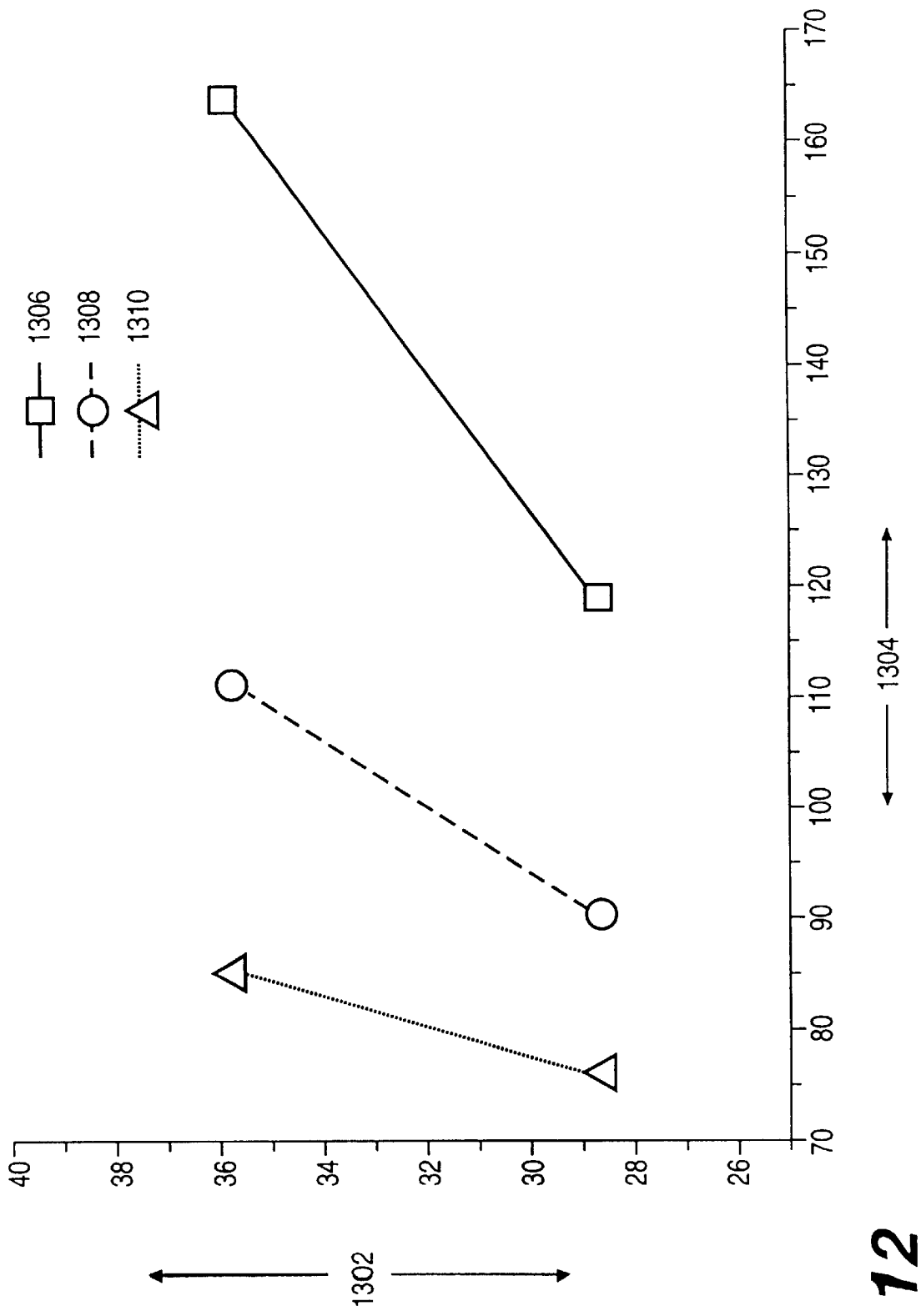
FIG. 12 graphs the relationship of second heart sound frequency vs. blood pressure.

Referring to FIG. 12, data from recent in-vivo testing on animal subjects at the Uniformed Services University of Health Sciences is shown. The subject had a pressure catheter emplaced to provide actual pressure readings, and the present invention detected, and processed the acoustic signature data from the second heart sounds. FIG. 12 plots the relationship between second heart sound A2 1302, and blood pressure 1304. As shown, where there is a rise in the frequency of second heart sound 1302, there is a corresponding rise in systolic pressure 1306, mean pressure 1308 and diastolic pressure 1310.

The subject whose pressure/frequency relationship is depicted in FIG. 12, had a resting systolic pressure of about 120 mm Hg, a resting diastolic pressure of about 77 mm Hg, and a predominant second heart sound frequency of 28.5 Hz. The mean blood pressure was thus about 90 mm Hg at 28.5 Hz. As the subject's blood pressure was artificially increased, the associated frequency components of the second heart sound correspondingly increased. Systolic pressure 1306 of the subject reached about 165 mm Hg, diastolic pressure 1310 reached about 85 mm Hg, and frequency of second heart sound 1302 reached 36. Mean pressure 1308 reached about 115 mm Hg. The slope of this mean pressure/frequency curve is approximately 2 mm Hg per Hz. This pressure/frequency correlation was demonstrated in each animal subject tested.

Across a population, measurement of the sound frequency associated with the closure of the aortic and pulmonary semilunar valves will allow an estimate of the mean systemic and pulmonary blood pressure. Specifically, using a range of pressure/frequency curves collected from population samples, the present invention will allow an estimate of the mean systemic and pulmonary pressure with a passive and non-invasive acoustic measurement of the acoustic signature of the semilunar valve closure. As an example, if the mean pressure data curve 1307 in FIG. 12 presented an accumulated average from the population, then measurement of a pulmonary semilunar valve closure sound frequency of 36 Hz 1309 would provide an estimate that the mean pulmonic pressure was 115 mm Hg 1311. In an otherwise asymptomatic patient, this might provide sufficient clinical justification for use of an invasive blood pressure catheter, with the attendant risk and cost, to confirm the pulmonic pressure.

Although the method of the present invention has been described in detail for purpose of illustration, it is understood that such detail is solely for that purpose, and variations can be made therein by those skilled in the art without departing from the spirit and scope of the invention. The apparatus, operation and method of the present invention is defined by the following claims.

What is claimed is:

1. A method of determining blood pressure comprising:
performing initialization procedures;
filtering physiologic signals, using a filter having a logarithmic characteristic, to create filtered physiologic signals;
acquiring the filtered physiologic signals;
acquiring background signals;
subtracting the background signals from the filtered physiologic signals, creating physiologic data;
processing the physiologic data forming a time domain output and a frequency domain output;
comparing the time domain output and the frequency domain output with a reference pattern and feature library; and
determining if an elevated blood pressure modality is indicated.

2. The method of determining blood pressure as claimed in claim 1, wherein performing initialization further comprises:
initializing a system;
calibrating the system;
selecting sensors in the system;
inputting patient parameters into the system; and
clearing system buffers.

3. The method of determining blood pressure as claimed in claim 1, wherein acquiring the filtered physiologic signals comprises acquiring filtered physiologic acoustic signals.

4. The method of determining blood pressure as claimed in claim 3, wherein electric signals are acquired in conjunction with the filtered physiologic acoustic signals.

5. The method of determining blood pressure as claimed in claim 1, wherein the filtered physiologic signals are in an analog form, the method further comprising:

converting, the filtered physiologic signals from the analog form to a digital form.

6. The method of determining blood pressure as claimed in claim 1, wherein the background signals are in an analog form, the method further comprising:

converting the background signals from the analog form to a digital form.

7. The method of determining blood pressure as claimed in claim 1, wherein processing the physiologic data comprises:

applying signal conditioning and time domain averaging to the physiologic data forming conditioned and averaged data;

formatting the conditioned and averaged data in an array creating formatted data;

transforming the formatted data to create transformed data;

integrating conditioned and averaged data with the transformed data, creating integrated data, wherein said integrated data has time domain components and frequency domain components;

passing the time domain components of the integrated data through a time domain correlator and feature extraction process, creating the time domain output; and passing the frequency domain components of the integrated data through a frequency domain correlator and feature extractor, creating the frequency domain output.

8. The method of determining blood pressure as claimed in claim 7, further comprising:

displaying the integrated data on a monitor.

9. The method of determining blood pressure as claimed in claim 1, further comprising:

updating the reference pattern and feature library.

10. A method of determining systemic blood pressure comprising:

monitoring the frequency of acoustic signals emitted by a valve selected from the group consisting of the pulmonary semilunar valve and the aortic semilunar valve, wherein the acoustic signals are detected using a sensor assembly, the sensor assembly comprising:
a housing having a front and a back;
an electronic module connected to the housing;
a shock dampener connected to the front of the housing;
a means for mounting connected to the housing;
an acoustic coupler connected to the mounting means, the acoustic coupler filtering out low frequency signals according to a logarithmic characteristic;
a transducer connected to the acoustic coupler; and
a cover connected to the back of the housing;

processing the acoustic signals, the processing comprising:

applying signal conditioning and time domain averaging to the acoustic signals to form conditioned and averaged data;

formatting the conditioned and averaged data in an array to create formatted data;

transforming the formatted data to create transformed data;

integrating the conditioned and averaged data with the transformed data, to create integrated data that has time domain components and frequency domain components;

passing the time domain components of the integrated data through a time domain correlator and feature extraction process to create a time domain output;

passing the frequency domain components of the integrated data through a frequency domain correlator and feature extractor, to create a frequency domain output;

comparing the time domain output and the frequency domain output with a reference pattern and feature library; and determining if an elevated blood pressure modality is indicated.

11. The method of determining systemic blood pressure using sonospectrography analysis as claimed in claim 10, further comprising:

acquiring background signals; and subtracting background signals from physiologic signals.

12. A sensor assembly for detecting physiological sounds comprising:

a housing having a front and a back;
an electronic module connected to the housing;
a shock dampener connected to the front of the housing;
a means for mounting connected to the shock dampener;
an acoustic coupler connected to the mounting means, the acoustic coupler filtering out low frequency signals according to a logarithmic characteristic;
a transducer connected to the acoustic coupler; and
a cover connected to the back of the housing.

13. The sensor assembly as claimed in claim 12, wherein the housing further comprises a sound deadening material.

14. The sensor assembly as claimed in claim 13, wherein the housing further comprises nickel plated aluminum.

15. The sensor assembly as claimed in claim 12, wherein the housing further comprises:

a rim having an inside and an outside, that is located on the periphery of the front of the housing;

a first indentation having an inside and an outside, that runs parallel and adjacent to the inside of the rim;

a second indentation that runs parallel and adjacent to the inside of the first indentation; and a bore, that is approximately centrally located within the second indentation.

16. The sensor assembly as claimed in claim 15, wherein the electronic module nests within the bore.

17. The sensor assembly as claimed in claim 12, wherein the shock dampener is an "O" ring.

18. The sensor assembly as claimed in claim 12, wherein the mounting means is a plastic mounting ring.

19. The sensor assembly as claimed in claim 12, wherein the transducer is a piezoelement.

20. A sensor assembly for detecting physiological sounds comprising:

a housing, having a front, a back, and an interior;
an electronic module that nests in the interior of the housing;
a first shock dampener connected to the front of the housing;
a first mounting means connected to the first shock dampener;
a first transducer connected to the first mounting means;
a first acoustic coupling connected to the first transducer, the first acoustic coupling filtering out low frequency signals according to a logarithmic characteristic;
a second shock dampener connected to the back of the housing;
a second mounting means connected to the second shock dampener;

a second transducer connected to the second mounting means; and a second acoustic coupling connected to the second transducer, the second acoustic coupling filtering out low frequency signals according to a logarithmic characteristic.

21. The sensor assembly as claimed in claim 20, wherein the housing further comprises a sound deadening material.

22. The sensor assembly as claimed in claim 21, wherein the housing further comprises nickel plated aluminum.

23. The sensor assembly as claimed in claim 20, wherein the housing further comprises:

a first rim having an inside and an outside, that is located on the periphery of the front of the housing;

a first indentation having an inside and an outside, that runs parallel and adjacent to the inside of the first rim;

a second indentation that runs parallel and adjacent to the inside of the first indentation;

a bore, that is approximately centrally located within the second indentation;

a second rim having an inside and an outside, that is located on the periphery of the back of the housing;

a third indentation having an inside and an outside, that runs parallel and adjacent to the inside of the second rim; and a fourth indentation, that runs parallel and adjacent to the inside of the third indentation.

24. The sensor assembly as claimed in claim 23, wherein the electronic module nests within the bore.

25. The sensor assembly as claimed in claim 23, wherein the first shock dampener is an "O" ring and the second shock dampener is an "O" ring.

26. The sensor assembly as claimed in claim 23, wherein the first mounting means is a plastic mounting ring and the second mounting means is a plastic mounting ring.

27. The sensor assembly as claimed in claim 23, wherein the first transducer is a piezoelement and the second transducer is a piezoelement.

* * * * *